(12) United States Patent
Iwakura et al.

(10) Patent No.: US 10,792,300 B2
(45) Date of Patent: Oct. 6, 2020

(54) DENDRITIC CELL IMMUNE RECEPTOR ACTIVATOR, METHOD FOR ACTIVATING DENDRITIC CELL IMMUNE RECEPTOR, OSTEOCLAST FORMATION INHIBITOR, METHOD FOR INHIBITING OSTEOCLAST FORMATION, DENDRITIC CELL DIFFERENTIATION/PROLIFERATION INHIBITOR, METHOD FOR INHIBITING DENDRITIC CELL DIFFERENTIATION/PROLIFERATION, CYTOKINE PRODUCTION INHIBITOR, METHOD FOR INHIBITING CYTOKINE PRODUCTION, THERAPEUTIC METHOD AND SCREENING METHOD

(71) Applicant: TOKYO UNIVERSITY OF SCIENCE FOUNDATION, Tokyo (JP)

(72) Inventors: Yoichiro Iwakura, Tokyo (JP); Tomonori Kaifu, Tokyo (JP); Rikio Yabe, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 0 days.

(21) Appl. No.: 15/323,748

(22) PCT Filed: Jul. 10, 2015

(86) PCT No.: PCT/JP2015/069960
§ 371 (c)(1),
(2) Date: Jan. 4, 2017

(87) PCT Pub. No.: WO2016/006700
PCT Pub. Date: Jan. 14, 2016

(65) Prior Publication Data
US 2017/0143754 A1    May 25, 2017

(30) Foreign Application Priority Data
Jul. 11, 2014 (JP) .................. 2014-143491

(51) Int. Cl.
*A61K 31/715* (2006.01)
*C12N 5/0784* (2010.01)
*G01N 33/50* (2006.01)

(52) U.S. Cl.
CPC .......... *A61K 31/715* (2013.01); *C12N 5/0639* (2013.01); *G01N 33/5047* (2013.01); *C12N 2501/50* (2013.01); *G01N 2333/705* (2013.01); *G01N 2400/38* (2013.01); *G01N 2500/02* (2013.01)

(58) Field of Classification Search
CPC ....................... A61K 31/715; C12N 5/0639
See application file for complete search history.

(56) References Cited

U.S. PATENT DOCUMENTS

| 5,834,423 A | 11/1998 | Koketsu et al. |
| 5,939,403 A | 8/1999 | Maruyama et al. |
| 2007/0207161 A1 | 9/2007 | Ralph |
| 2009/0202440 A1 | 8/2009 | Iwakura et al. |
| 2013/0058957 A1 | 3/2013 | Iwakura et al. |

FOREIGN PATENT DOCUMENTS

| JP | 2000139463 A | 5/2000 |
| JP | 2007508328 A | 4/2007 |
| JP | 2008029319 A | 2/2008 |
| JP | 2009019044 A | 1/2009 |
| WO | WO-96/02255 A1 | 2/1996 |
| WO | WO-2008/001498 A1 | 1/2008 |
| WO | WO-2011/105424 A1 | 9/2011 |

OTHER PUBLICATIONS

Liu et al., Human Immunology, 2015, 76, p. 808-811. (Year: 2015).*
Jongbloed et al., J. Immunology, 2009, 182, p. 963-968. (Year: 2009).*
Fujikado et al., "Dcir Deficiency Causes Development of Autoimmune Diseases in Mice Due to Excess Expansion of Dendritic Cells", Nature Medicine, vol. 14, No. 2, Feb. 2008, 5 pages.
Yabe et al., "Quantitative Interaction Analysis Between DC-Sign-Related Lectins and Oligosaccharides: Discovery of Their Specificities to Agalactosylated N-Glycans", Journal of Japanese Biochemical Society, Shoroku CD, Rombunno 4P-108, 2009, 2 pages.
Yabe et al., "Frontal Affinity Chromatography Analysis of Constructs of DC-SIGN, DC-SIGNR and LSECtin Extend Evidence for Affinity fo Agalactosylated N-glycans", FEBS Journal, 277, 2010, pp. 4010-4026.
Riboldi et al., "Human C-type Lectin Domain Family 4, Member C(CLEC4C/BDCA-2/CD303) is a Receptor for Asialo-galactosyl-oligosaccharides", Journal of Biological Chemistry, vol. 286, No. 41, Oct. 14, 2011, 6 pages.
Search Report and Written Opinion in International Application No. PCT/JP2015/069960 dated Oct. 13, 2015, 9 pages.

* cited by examiner

*Primary Examiner* — Jonathan S Lau
(74) *Attorney, Agent, or Firm* — Marshall, Gerstein & Borun LLP

(57) ABSTRACT

A dendritic cell immune receptor activator, comprising a compound having a sugar chain as an active ingredient, the sugar chain having a basic structure represented by the following formula:

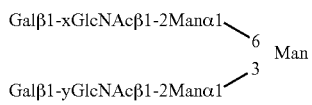

wherein, in the formula, a sialic acid does not exist at two non-reducing terminals, and each of x and y independently represents 3 or 4.

7 Claims, 28 Drawing Sheets

Specification includes a Sequence Listing.

b.

c.

d.

e.

d.

e.

c.

d.

e.

f.

a.

SEQUENCE LISTING

```
<160> NUMBER OF SEQ ID NOS: 36

<210> SEQ ID NO 1
<211> LENGTH: 34
<212> TYPE: DNA
<213> ORGANISM: Artificial Sequence
<220> FEATURE:
<223> OTHER INFORMATION: Primer for PCR

<400> SEQUENCE: 1
cgggatccca ccatggcttc agaaatcact tatg                           34

<210> SEQ ID NO 2
<211> LENGTH: 28
<212> TYPE: DNA
<213> ORGANISM: Artificial Sequence
<220> FEATURE:
<223> OTHER INFORMATION: Primer for PCR

<400> SEQUENCE: 2
cggaattctc ataagtttat tttcttca                                  28

<210> SEQ ID NO 3
<211> LENGTH: 33
<212> TYPE: DNA
```

```
<213> ORGANISM: Artificial Sequence
<220> FEATURE:
<223> OTHER INFORMATION: Primer for PCR

<400> SEQUENCE: 3
cacttttgca gaagtgaagt tcaagaatga atc                          33

<210> SEQ ID NO 4
<211> LENGTH: 33
<212> TYPE: DNA
<213> ORGANISM: Artificial Sequence
<220> FEATURE:
<223> OTHER INFORMATION: Primer for PCR

<400> SEQUENCE: 4
atttctgaag ccatggtggg atccttggtt aac                          33

<210> SEQ ID NO 5
<211> LENGTH: 22
<212> TYPE: DNA
<213> ORGANISM: Artificial Sequence
<220> FEATURE:
<223> OTHER INFORMATION: Primer for PCR

<400> SEQUENCE: 5
cctggtgatt ctatgctgtg gt                                      22

<210> SEQ ID NO 6
<211> LENGTH: 24
<212> TYPE: DNA
<213> ORGANISM: Artificial Sequence
<220> FEATURE:
<223> OTHER INFORMATION: Primer for PCR

<400> SEQUENCE: 6
gtcagaagag agccttgttc cttc                                    24

<210> SEQ ID NO 7
<211> LENGTH: 20
<212> TYPE: DNA
<213> ORGANISM: Artificial Sequence
<220> FEATURE:
<223> OTHER INFORMATION: Primer for PCR

<400> SEQUENCE: 7
ttcaccacca tggagaaggc                                         20

<210> SEQ ID NO 8
<211> LENGTH: 20
<212> TYPE: DNA
<213> ORGANISM: Artificial Sequence
<220> FEATURE:
<223> OTHER INFORMATION: Primer for PCR

<400> SEQUENCE: 8
ggcatggact gtggtcatga                                         20

<210> SEQ ID NO 9
<211> LENGTH: 22
<212> TYPE: DNA
<213> ORGANISM: Artificial Sequence
<220> FEATURE:
<223> OTHER INFORMATION: Primer for PCR

<400> SEQUENCE: 9
catttccctt atctcgccct gg                                      22
```

```
<210> SEQ ID NO 10
<211> LENGTH: 19
<212> TYPE: DNA
<213> ORGANISM: Artificial Sequence
<220> FEATURE:
<223> OTHER INFORMATION: Primer for PCR

<400> SEQUENCE: 10
gcatgagtgt ccaagatcc                                              19

<210> SEQ ID NO 11
<211> LENGTH: 30
<212> TYPE: DNA
<213> ORGANISM: Artificial Sequence
<220> FEATURE:
<223> OTHER INFORMATION: Primer for PCR

<400> SEQUENCE: 11
ataagatctc aaaagtactc tcaacttctt                                  30

<210> SEQ ID NO 12
<211> LENGTH: 28
<212> TYPE: DNA
<213> ORGANISM: Artificial Sequence
<220> FEATURE:
<223> OTHER INFORMATION: Primer for PCR

<400> SEQUENCE: 12
ataagatctt aagtttattt tcttcatc                                    28

<210> SEQ ID NO 13
<211> LENGTH: 27
<212> TYPE: DNA
<213> ORGANISM: Artificial Sequence
<220> FEATURE:
<223> OTHER INFORMATION: Primer for PCR

<400> SEQUENCE: 13
aatggtgctc ccagcagtgg caatgaa                                     27

<210> SEQ ID NO 14
<211> LENGTH: 27
<212> TYPE: DNA
<213> ORGANISM: Artificial Sequence
<220> FEATURE:
<223> OTHER INFORMATION: Primer for PCR

<400> SEQUENCE: 14
tgtaagaccg tgttaccacg agggtca                                     27

<210> SEQ ID NO 15
<211> LENGTH: 27
<212> TYPE: DNA
<213> ORGANISM: Artificial Sequence
<220> FEATURE:
<223> OTHER INFORMATION: Primer for PCR

<400> SEQUENCE: 15
gagcccgcta gtggcaatga aaaatgt                                     27

<210> SEQ ID NO 16
<211> LENGTH: 27
<212> TYPE: DNA
<213> ORGANISM: Artificial Sequence
<220> FEATURE:
```

<223> OTHER INFORMATION: Primer for PCR

<400> SEQUENCE: 16
accgtgttac cactcgggcg atcaccg        27

<210> SEQ ID NO 17
<211> LENGTH: 33
<212> TYPE: DNA
<213> ORGANISM: Artificial Sequence
<220> FEATURE:
<223> OTHER INFORMATION: Primer for PCR

<400> SEQUENCE: 17
ggtgctcccg ctagtggcaa tgaaaaatgt gct        33

<210> SEQ ID NO 18
<211> LENGTH: 33
<212> TYPE: DNA
<213> ORGANISM: Artificial Sequence
<220> FEATURE:
<223> OTHER INFORMATION: Primer for PCR

<400> SEQUENCE: 18
tagtgtaaga ccgtgttacc acgagggcga tca        33

<210> SEQ ID NO 19
<211> LENGTH: 18
<212> TYPE: DNA
<213> ORGANISM: Artificial Sequence
<220> FEATURE:
<223> OTHER INFORMATION: Primer for PCR

<400> SEQUENCE: 19
cagcagccca aaatgcct        18

<210> SEQ ID NO 20
<211> LENGTH: 20
<212> TYPE: DNA
<213> ORGANISM: Artificial Sequence
<220> FEATURE:
<223> OTHER INFORMATION: Primer for PCR

<400> SEQUENCE: 20
ttttgagcca ggacagctga        20

<210> SEQ ID NO 21
<211> LENGTH: 20
<212> TYPE: DNA
<213> ORGANISM: Artificial Sequence
<220> FEATURE:
<223> OTHER INFORMATION: Primer for PCR

<400> SEQUENCE: 21
gccaagtacc agctttccag        20

<210> SEQ ID NO 22
<211> LENGTH: 20
<212> TYPE: DNA
<213> ORGANISM: Artificial Sequence
<220> FEATURE:
<223> OTHER INFORMATION: Primer for PCR

<400> SEQUENCE: 22
agggtcgagg tgacactagg        20

-continued

```
<210> SEQ ID NO 23
<211> LENGTH: 20
<212> TYPE: DNA
<213> ORGANISM: Artificial Sequence
<220> FEATURE:
<223> OTHER INFORMATION: Primer for PCR

<400> SEQUENCE: 23
gcctccccat ttacatctgc                                               20

<210> SEQ ID NO 24
<211> LENGTH: 19
<212> TYPE: DNA
<213> ORGANISM: Artificial Sequence
<220> FEATURE:
<223> OTHER INFORMATION: Primer for PCR

<400> SEQUENCE: 24
ctcctcgcct tcgttgttg                                                19

<210> SEQ ID NO 25
<211> LENGTH: 20
<212> TYPE: DNA
<213> ORGANISM: Artificial Sequence
<220> FEATURE:
<223> OTHER INFORMATION: Primer for PCR

<400> SEQUENCE: 25
gccaagtacc aggtttccag                                               20

<210> SEQ ID NO 26
<211> LENGTH: 20
<212> TYPE: DNA
<213> ORGANISM: Artificial Sequence
<220> FEATURE:
<223> OTHER INFORMATION: Primer for PCR

<400> SEQUENCE: 26
agggtcgagg tgacactagg                                               20

<210> SEQ ID NO 27
<211> LENGTH: 19
<212> TYPE: DNA
<213> ORGANISM: Artificial Sequence
<220> FEATURE:
<223> OTHER INFORMATION: Primer for PCR

<400> SEQUENCE: 27
gaacccgaga gggaccttc                                                19

<210> SEQ ID NO 28
<211> LENGTH: 21
<212> TYPE: DNA
<213> ORGANISM: Artificial Sequence
<220> FEATURE:
<223> OTHER INFORMATION: Primer for PCR

<400> SEQUENCE: 28
gaggcagtag gcaccttttg t                                             21

<210> SEQ ID NO 29
<211> LENGTH: 20
<212> TYPE: DNA
<213> ORGANISM: Artificial Sequence
<220> FEATURE:
<223> OTHER INFORMATION: Primer for PCR
```

<400> SEQUENCE: 29
agccagaaaa caaggctgaa					20

<210> SEQ ID NO 30
<211> LENGTH: 20
<212> TYPE: DNA
<213> ORGANISM: Artificial Sequence
<220> FEATURE:
<223> OTHER INFORMATION: Primer for PCR

<400> SEQUENCE: 30
ggctgggtgt ccagtagtgt					20

<210> SEQ ID NO 31
<211> LENGTH: 20
<212> TYPE: DNA
<213> ORGANISM: Artificial Sequence
<220> FEATURE:
<223> OTHER INFORMATION: Primer for PCR

<400> SEQUENCE: 31
gtaggtgcga ctgggatgtt					20

<210> SEQ ID NO 32
<211> LENGTH: 20
<212> TYPE: DNA
<213> ORGANISM: Artificial Sequence
<220> FEATURE:
<223> OTHER INFORMATION: Primer for PCR

<400> SEQUENCE: 32
agtgaggcca actcagccta					20

<210> SEQ ID NO 33
<211> LENGTH: 21
<212> TYPE: DNA
<213> ORGANISM: Artificial Sequence
<220> FEATURE:
<223> OTHER INFORMATION: Primer for PCR

<400> SEQUENCE: 33
cagcatcgct ctgttcctgt a					21

<210> SEQ ID NO 34
<211> LENGTH: 21
<212> TYPE: DNA
<213> ORGANISM: Artificial Sequence
<220> FEATURE:
<223> OTHER INFORMATION: Primer for PCR

<400> SEQUENCE: 34
ctgcgttttc atggagtctc a					21

<210> SEQ ID NO 35
<211> LENGTH: 19
<212> TYPE: DNA
<213> ORGANISM: Artificial Sequence
<220> FEATURE:
<223> OTHER INFORMATION: Primer for PCR

<400> SEQUENCE: 35
gggcgttacc tggagatcg					19

<210> SEQ ID NO 36
<211> LENGTH: 23

```
<212> TYPE: DNA
<213> ORGANISM: Artificial Sequence
<220> FEATURE:
<223> OTHER INFORMATION: Primer for PCR

<400> SEQUENCE: 36
gagaagaacc catctggaca ttt                                           23
```

DENDRITIC CELL IMMUNE RECEPTOR ACTIVATOR, METHOD FOR ACTIVATING DENDRITIC CELL IMMUNE RECEPTOR, OSTEOCLAST FORMATION INHIBITOR, METHOD FOR INHIBITING OSTEOCLAST FORMATION, DENDRITIC CELL DIFFERENTIATION/PROLIFERATION INHIBITOR, METHOD FOR INHIBITING DENDRITIC CELL DIFFERENTIATION/PROLIFERATION, CYTOKINE PRODUCTION INHIBITOR, METHOD FOR INHIBITING CYTOKINE PRODUCTION, THERAPEUTIC METHOD AND SCREENING METHOD

TECHNICAL FIELD

The invention relates to a dendritic cell immune receptor activator, a method for activating a dendritic cell immune receptor, an osteoclast formation inhibitor, a method for inhibiting osteoclast formation, a dendritic cell differentiation/proliferation inhibitor, a method for inhibiting dendritic cell differentiation/proliferation, a cytokine production inhibitor, a method for inhibiting cytokine production, a therapeutic method, and a screening method.

BACKGROUND ART

A dendritic cell immune receptor (hereinafter, also referred to as DCIR) is a membrane protein that expresses in a cell such as a dendritic cell, which is a major antigen presentation cell, and an osteoclastic cell, which is a bone resorption cell. A DCIR has a carbohydrate-recognition domain (CRD) in the extracellular region, and an immuno-receptory tyrosine-based inhibitory motif (ITIM) in the intracellular region.

The inventors have succeeded in preparing a mouse lacking a gene of a DCIR (Dcir−/− mouse), and reported that the mouse spontaneously develops with aging autoimmune disorders such as Sjogren's syndrome or enthesitis (see, for example, Japanese Patent Application Laid-Open (JP-A) Nos. 2008-29319 and 2009-19044). The inventors also reported that the Dcir−/− mouse was highly susceptible to collagen-induced arthritis, and this is due to excessive proliferation and differentiation of dendritic cells (see, for example, Fujikado et al., Nat. Med., 2008).

As described above, a DCIR is considered to negatively regulate the formation of osteoclasts, differentiation or proliferation of dendritic cells, and production of pro-inflammatory cytokines. Therefore, identification of a DCIR-specific ligand will provide a means for suppressing the symptoms of bone metabolic diseases or autoimmune diseases. Further, since dendritic cells play a major role in the immune system, a DCIR-specific ligand is expected to exhibit a therapeutic effect in allergy diseases and the like. In connection with the above, the inventors have found that keratan sulfate II (KS-II) mediates a signaling pathway into osteoclasts via SHP-1, as an internal ligand that specifically binds to a DCIR (see, for example, International Publication No. WO 2011/105424).

SUMMARY OF THE INVENTION

Problem to be Solved by the Invention

Although there are some reports on DCIR-specific ligands, the behavior thereof has yet to be proven in various aspects. Further, identifying DCIR-specific ligands of different kinds will be beneficial in increasing the therapeutic options for diseases in which regulation of the biological mechanism by a DCIR may be effective.

In view of the above, the invention aims to provide a novel dendritic cell immune receptor activator, a novel method for activating dendritic cell immune receptor, a novel osteoclast formation inhibitor, a novel method for inhibiting osteoclast formation, a novel dendritic cell differentiation/proliferation inhibitor, a novel method for inhibiting dendritic cell differentiation/proliferation, a novel cytokine production inhibitor, a novel method for inhibiting cytokine production, a novel therapeutic method, and a novel screening method.

Means for Solving the Problem

The following are specific means for solving the problem.

<1> A dendritic cell immune receptor activator, comprising a compound having a sugar chain as an active ingredient, the sugar chain having a basic structure represented by the following formula:

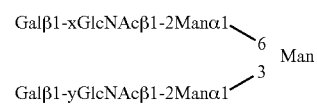

wherein, in the formula, a sialic acid does not exist at two non-reducing terminals, and each of x and y independently represents 3 or 4.

<2> A method for activating a dendritic cell immune receptor, comprising causing the dendritic cell immune receptor activator according to <1> to contact a dendritic cell immune receptor of a cell.

<3> An osteoclast formation inhibitor, comprising a compound having a sugar chain as an active ingredient, the sugar chain having a basic structure represented by the following formula:

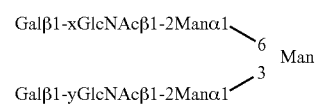

wherein, in the formula, a sialic acid does not exist at two non-reducing terminals, and each of x and y independently represents 3 or 4.

<4> A method for inhibiting osteoclast formation, comprising causing the osteoclast formation inhibitor according to <3> to contact a dendritic cell immune receptor of an osteoclast.

<5> A dendritic cell differentiation/proliferation inhibitor, comprising a compound having a sugar chain as an active ingredient, the sugar chain having a basic structure represented by the following formula:

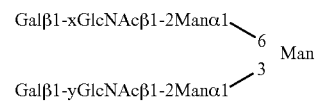

wherein, in the formula, a sialic acid does not exist at two non-reducing terminals, and each of x and y independently represents 3 or 4.

<6> A method for inhibiting dendritic cell differentiation/proliferation, comprising causing the dendritic cell differentiation/proliferation inhibitor according to <5> to contact a dendritic cell immune receptor of a dendritic cell.

<7> A cytokine production inhibitor, comprising a compound having a sugar chain as an active ingredient, the sugar chain having a basic structure represented by the following formula:

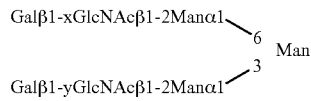

wherein, in the formula, a sialic acid does not exist at two non-reducing terminals, and each of x and y independently represents 3 or 4.

<8> A method for inhibiting cytokine production, comprising causing the cytokine production inhibitor according to <7> to contact a dendritic cell immune receptor of a dendritic cell.

<9> A therapeutic method, comprising administering the dendritic cell immune receptor activator according to <1> to a patient having a bone metabolism disease, an autoimmune disease or an allergy disease.

<10> A screening method, comprising screening a dendritic cell immune receptor activator or a dendritic cell immune receptor antagonist, by measuring an ability of a test substance to bind to a dendritic cell immune receptor, under the presence of a compound having a sugar chain as an active ingredient, the sugar chain having a basic structure represented by the following formula, or by using the compound as a control:

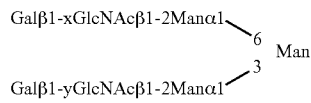

wherein, in the formula, a sialic acid does not exist at two non-reducing terminals, and each of x and y independently represents 3 or 4.

Effect of the Invention

According to the invention, it is possible to provide a novel dendritic cell immune receptor activator, a novel method for activating dendritic cell immune receptor, a novel osteoclast formation inhibitor, a novel method for inhibiting osteoclast formation, a novel dendritic cell differentiation/proliferation inhibitor, a novel method for inhibiting dendritic cell differentiation/proliferation, a novel cytokine production inhibitor, a novel method for inhibiting cytokine production, a novel therapeutic method, and a novel screening method.

EMBODIMENTS FOR IMPLEMENTING THE INVENTION

Figure 1:
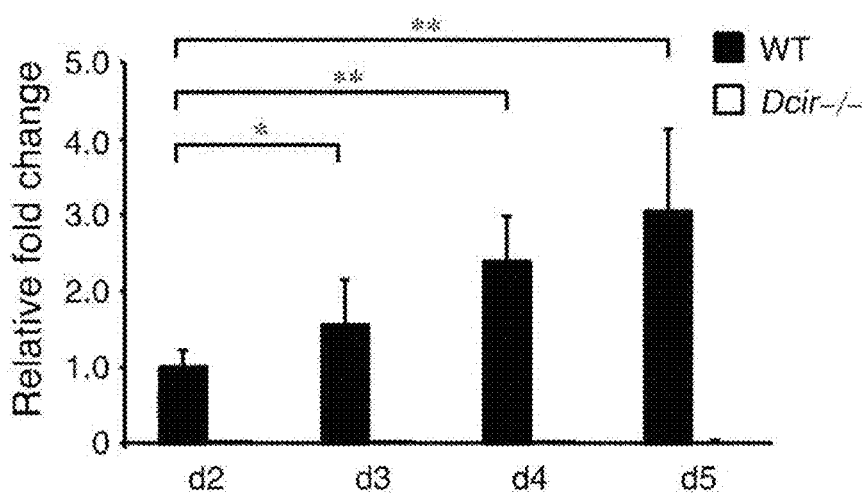
FIG. 1 shows the data of quantification of the DCIR mRNA during osteoclast formation and the results of flow cytometric detection of the DCIR expression in wild-type and Dcir−/− osteoclasts. The line with a right-side peak indicates wild-type and the line with a left-side peak indicates Dcir−/−. The gray area indicates an isotype control. The data are representative of two or three independent experiments. The error bars represent the means±s.d. of triplicate cultures. *P<0.05; **P<0.01.

In the following, embodiments of the invention are explained. The explanation and the examples are intended to illustrate the invention, and the scope of the invention is not restricted by them.

In the specification, the numerical range represented by A to B includes A and B as the minimum value and the maximum value, respectively.

The DCIR activation refers to bringing the activity of a DCIR to be higher by contacting the DCIR activator to the DCIR, as compared to the case in which the DCIR is not contacted with the DCIR activator.

The osteoclast formation inhibition refers to bringing the formation of osteoclasts to be inhibited by contacting the osteoclast formation inhibitor to a DCIR, as compared to the case in which the DCIR is not contacted with the osteoclast formation inhibitor.

The cytokine production inhibition refers to bringing the production of cytokine to be inhibited by contacting the cytokine production inhibitor to a DCIR, as compared to the case in which the DCIR is not contacted with the cytokine production inhibitor.

The dendritic cell differentiation/proliferation inhibition refers to bringing the differentiation/proliferation of dendritic cells to be inhibited by contacting the dendritic cell differentiation/proliferation inhibitor to a DCIR, as compared to the case in which the DCIR is not contacted with the dendritic cell differentiation/proliferation inhibitor.

The therapy refers not only to eliminating the symptoms of a disease to be treated, but also to suppressing aggravation of the symptoms or alleviating the symptoms.

<DCIR Activator>

The DCIR activator includes a compound having a sugar chain having a basic structure represented by the following formula as an active ingredient.

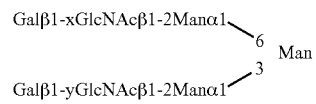

wherein in the formula, a sialic acid does not exist at two non-reducing terminals, and each of x and y independently represents 3 or 4.

There has been no report that the compound having a structure as specified above is a ligand that specifically binds to a DCIR. In the following, the compound is also referred to as a specific sugar chain-containing compound.

The structure of the sugar chain of the specific sugar chain-containing compound is not limited as long as the effect of the invention is achieved. For example, the sugar chain may have a branched chain or may be added with fucose at any position of the basic structure. However, a sialic acid does not exist at the two non-reducing terminals of the basic structure. Examples of the structure of the sugar chain include the following.

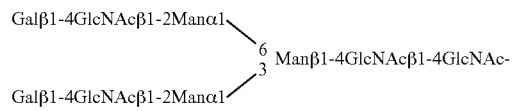

-continued

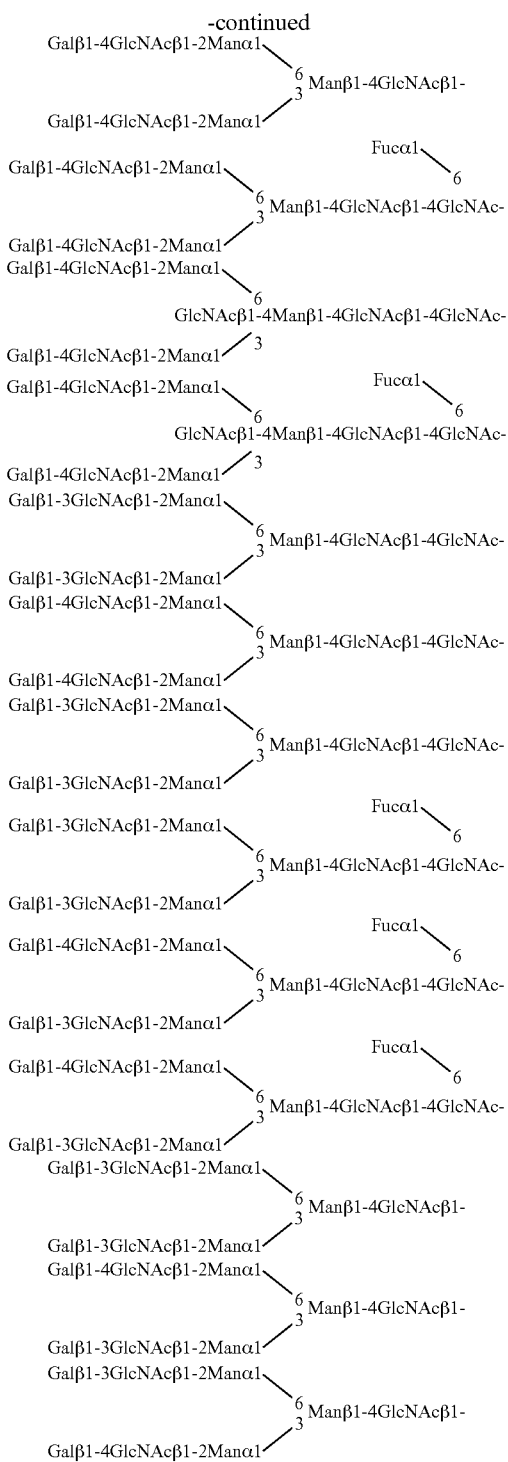

The method for preparing the specific sugar chain-containing compound is not specifically limited. For example, the specific sugar chain-containing compound may be collected from a living body or may be manufactured by a biotechnological or organic synthetic process.

The structure or the kind of the specific sugar chain-containing compound is not specifically limited, as long as the effect of the invention is achieved. For example, the specific sugar chain-containing compound may be a compound having a structure that is the same with or similar to a structure of a compound derived from a living body, or may be a compound that is not derived from a living body. From the viewpoint of the compatibility with a living body, the specific sugar chain-containing compound is preferably a compound having a structure that is the same with or similar to a structure of a compound derived from a living body. Examples of the compound derived from a living body include a protein (including a peptide).

Examples of the protein as the specific sugar chain-containing compound include a compound in which the reducing end of the sugar chain is bound to transferrin, acid glucoprotein, fetuin, egg white protein derived from chicken, and the like.

Examples of the compound not derived from a living body as the specific sugar chain-containing compound include a compound in which the reduing end of the sugar chain is bound to polyacrylamide (PAA), paranitrophenyl phenol (pNP), aminopyridine (PA) and the like.

The specific sugar chain-containing compound may be subjected to modification of various kinds, according to purposes. Examples of the modification include converting to a polymer (carriers such as microbeads, ceramic beads, proteins such as BSA and HSA, including peptides), amino gorup modification (such as biotinylation, myristoylation, palmitoylation, acetylation and maleimidation), carboxy group modification (such as amidation and esterification), thiol group modification (such as farnesylation, geranylation, methylation and palmitoylation), hydroxy group modification (such as phosphorylation, sulfation, octanoylation, palmitoylation, palmitoleoylation and acetylation), fluorescence labelling, pegylation, and introduction of unnatural amino acids, D-amino acids, spacers or the like.

The DCIR activator may include a component other than the specific sugar chain-containing compound, according to purposes. Examples of the compound other than the specific sugar chain-containing compound include a medium or a formulation additive used for preparing the DCIR activator. Examples of the formulation additive include a diluent, a disintegrant, a binder, a lubricant, a surfactant, a buffer, a solubilizing agent, a stabilizer, a tonicity agent, a suspending agent, an emulsifier, and a solvent.

The DCIR activator may be in any form according to purposes. For Example, the DCIR activator may be in a form suitable for oral administration such as tables, granulated particles, powders, capsules, suspensions, syrups, emulsions and limonades, ampres for injection, lyophilized powder for injection, and powders for lung administration.

<Method for Activating DCIR>

The method for activating a DCIR includes contacting the DCIR activator to a DCIR of a cell. The method for contacting the DCIR activator to a cell is not specifically limited, and examples thereof include oral administration, intravenous administration and surgical treatments such as indwelling. The amount of the DCIR activator to be contacted with a DCIR is not specifically limited, and may be selected in view of the state of activity of a DCIR, the degree of intended activation, the kind or the amount of a component used with the specific sugar chain-containing compound, and the like.

Exemplary effects that can be expected by activating a DCIR by the method for activating a DCIR include inhibiting a biological mechanism that is negatively regulated by a DCIR by intentionally activating the same, when the biological mechanism is an excessive state for some reason. Examples of the biological mechanism to be negatively regulated by a DCIR include formation of osteoclasts, osteoclast proliferation response, production of cytokine, dendritic cell proliferation response, regulation of functions of dendritic cells, monocyte response, and regulation of functions of neutrophils. Therefore, the method of activating a DCIR can achieve inhibition of formation of ostelclasts, inhibition of differentiation/proliferation of dendritic cells, inhibition of cytokine production, and the like.

The type of the cell having a DCIR to be activated by the method for activating a DCIR is not specifically limited, and examples thereof include dendritic cells, osteoclasts, macrophages, monocytes and neutrophils.

<Osteoclast Formation Inhibitor>

The osteoclast formation inhibitor includes the specific sugar chain-containing compound as an active ingredient. The specific sugar chain-containing compound functions as a ligand that activates a DCIR. A DCIR negatively regulates the formation of ostelclasts. Therefore, formation of osteoclasts can be inhibited by activating a DCIR by contacting the osteoclast formation inhibitor to the DCIR.

Specific embodiments of the osteoclast formation inhibitor and the specific sugar chain-containing compound included in the osteoclast formation inhibitor as an active ingredient may be the same as the specific embodiments of the DCIR activator and the specific sugar chain-containing compound included in the DCIR activator as an active ingredient, as described above.

<Method for Inhibiting Osteoclast Formation>

The method for inhibiting osteoclast formation include contacting the osteoclast formation inhibitor to a DCIR of an osteoclast. The method for contacting the osteoclast formation inhibitor to a DCIR is not specifically limited, and examples thereof include oral administration, intravenous administration and surgical treatments such as indwelling. The amount of the DCIR activator to be contacted with the DCIR is not specifically limited, and may be selected in view of the state of osteoclast formation, the degree of intended inhibition of osteoclast formation, the kind or the amount of a component used with the specific sugar chain-containing compound, and the like.

Exemplary effects that can be expected by inhibiting the formation of osteoclasts by the method of inhibiting osteoclast formation include recovering a balance between the bone formation by osteoblasts and the bone resorption by the osteoclasts, when it is disrupted for some reason and the bone resorption by osteoclasts is relatively predominant, by intentionally inhibiting the formation of osteoclasts, and thus maintaining the homeostasis of bones.

<Dendritic Cell Differentiation/Proliferation Inhibitor>

The dendritic cell differentiation/proliferation inhibitor includes the specific sugar chain-containing compound as an active ingredient. The specific sugar chain-containing compound functions as a ligand that activates a DCIR. A DCIR negatively regulates the differentiation/proliferation of dendtritic cells. Therefore, differentiation/proliferation of dendritic cells can be inhibited by activating a DCIR by contacting the dendtiric cell differentiation/proliferation inhibitor to a DCIR.

Specific embodiments of the dendritic cell differentiation/proliferation inhibitor and the specific sugar chain-containing compound included in the dendritic cell differentiation/proliferation inhibitor as an active ingredient may be the same as the specific embodiments of the DCIR activator and the specific sugar chain-containing compound included in the DCIR activator as an active ingredient, as described above.

<Method for Inhibiting Dendtiric Cell Differentiation/Proliferation>

The method for inhibiting dendtiric cell differentiation/proliferation include contacting the dendtiric cell differentiation/proliferation inhibitor to a DCIR of a dendritic cell. The method for contacting the dendtiric cell differentiation/proliferation inhibitor to a DCIR is not specifically limited, and examples thereof include oral administration, intravenous administration and surgical treatments such as indwelling. The amount of the dendtiric cell differentiation/proliferation inhibitor to be contacted with a DCIR is not specifically limited, and may be selected in view of the state of differentiation/proliferation of dendritic cells, the degree of intended inhibition of differentiation/proliferation of dendritic cells, and the like.

<Cytokine Production Inhibitor>

The cytokine production inhibitor includes the specific sugar chain-containing compound as an active ingredient. The specific sugar chain-containing compound functions as a ligand that activates a DCIR. A DCIR negatively regulates the production of cytokines of specific kinds. Therefore, production of a cytokine can be inhibited by activating a DCIR by contacting the cytokine production inhibitor to a DCIR.

Specific embodiments of the cytokine production inhibitor and the specific sugar chain-containing compound included in the cytokine production inhibitor as an active ingredient may be the same as the specific embodiments of the DCIR activator and the specific sugar chain-containing compound included in the DCIR activator as an active ingredient, as described above.

<Method for Inhibiting Dendtiric Cell Differentiation/Proliferation>

The method for inhibiting cytokine production include contacting the cytokine production inhibitor to a DCIR of an dendritic cell. The method for contacting the cytokine production inhibitor to a DCIR is not specifically limited, and examples thereof include oral administration, intravenous administration and surgical treatments such as indwelling. The amount of the cytokine production inhibitor to be contacted with a DCIR is not specifically limited, and may be selected in view of the state of cytokine production, the degree of intended inhibition of cytokine production, the kind or the amount of a component used with the specific sugar chain-containing compound, and the like.

Exemplary effects that can be expected by inhibiting the cytokine production by the method of inhibiting cytokine production include alleviating excessive immune reaction or inflammation by intentionally inhibiting production of a cytokine that is negatively regulated by a DCIR, when the production of the cytokine is increased for some reason and the immune reaction or the inflammation is caused by the same.

The type of the cytokine whose production is inhibited by the method of inhibiting cytokine production is not specifically limited, and examples thereof include IFN-γ, IL-6, IL-12, IL-23, IL-1, IL-17 and IL-17F.

<Therapeutic Method>

The therapeutic method includes administrating the DCIR activator to a patient having a bone metabolism disease, an autoimmune disease or an allergy disease.

As described above, when the DCIR activator is contacted with a DCIR, the specific sugar chain-containing compound included in the DCIR activator as an active ingredient functions as a ligand that activates a DCIR. As a result, a biological mechanism that is negatively regulated by a DCIR can be intentionally inhibited. Examples of the biological mechanism include formation of osteoclasts, production of cytokines, and the like.

Accordingly, the therapeutic method is effective as a therapeutic method for various bone metabolism diseases that relate to excessive bone resorption, and various autoimmune diseases and allergy diseases accompanied by excessive immune reaction or inflammation of pro-inflammatory cytokines. Further, since the specific sugar chain-containing compound specifically functions with regard to a DCIR and inhibit functions of osteoclasts, dendritic cells or the like, the medical active sites can be localized and a therapeutic method with less side effects can be provided.

Examples of the bone metabolism disease include osteoarthritis, spondylarthrosis, osteoprosis, Paget's disease of bone, osteitis deformans, osteopetrosis and a gum disease. Examples of the autoimmune disease include arthrorheumatism, multiple sclerosis, Guillain-Barre syndrome, Goodpasture's syndrome, type I diabetes, thyroiditis, colitis ulcerosa and Sjogren's syndrome. Examples of the allergy disease include asthma, atopic dermatitis, conjunctiva inflammation, food allergy, anaphylaxis, contact dermatitis, allergic rhinitis and chronic glomerulonephritis.

In the therapeutic method, the method for administering the DCIR activator to a patient is not specifically limited, and examples thereof include oral administration, intravenous administration and surgical treatments such as indwelling. The amount of the DCIR activator to be administered is not specifically limited, and may be selected in view of the type or the state of the disease, the age or the physical size of the patient, the state of the DCIR activation, the degree of the intended DCIR activation, the kind or the amount of a component used with the specific sugar chain-containing compound, and the like.

Specific embodiments of the DCIR activator to be administered to a patient and the specific sugar chain-containing compound included in the DCIR activator may be the same as the specific embodiments of the DCIR activator and the specific sugar chain-containing compound included in the DCIR activator as an active ingredient, as described above.

<Screening Method>

The screening method include screening a DCIR activator or a DCIR antagonist, by measuring an ability of a test substance to bind to a DCIR, under the presence of the specific sugar chain-containing compound or by using the specific sugar chain-containing compound as a control.

By measuring an ability of the test substance to bind to a DCIR and comparing with that of the specific sugar chain-containing compound, whether the test compound is a DCIR activator or a DCIR antagonist can be determined. The measurement of the ability of binding to a DCIR can be performed either in vitro or in vivo. When the screening is performed in vivo, the measurement results may be compared based on the amount of formation of osteoclasts, the degree of differentiation/proliferation of dendritic cells, the amount of production of cytokines, and the like.

EXAMPLES

In the following, the invention is described in further detail with reference to the examples. The material, amount, content, procedure or the like may be changed without departing from the scope of the invention. Accordingly, the scope of the invention should not be construed in a limited manner by the specific embodiments as described below.

Experiment 1

Figure 2:
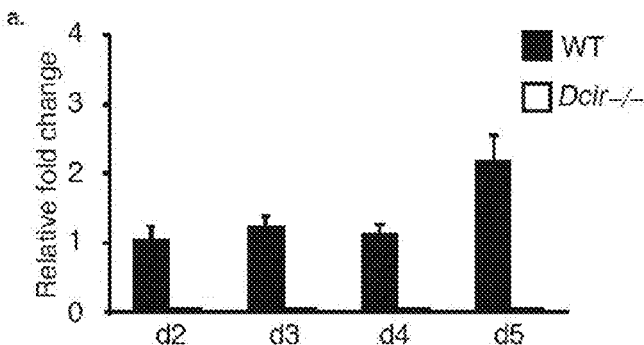
FIG. 2 is a graph showing the DCIR expression in BMMs cultured in the presence of M-CSF. The data are obtained by calculating the result of real-time PCR for the indicated days by the $2^{-ddct}$ method, and shown as a relative value, compared to that of macrophages at day 2 culture. The data are representative of at least three independent experiments. The errors represent the means±s.d. of triplicate cultures.
Figure 3:
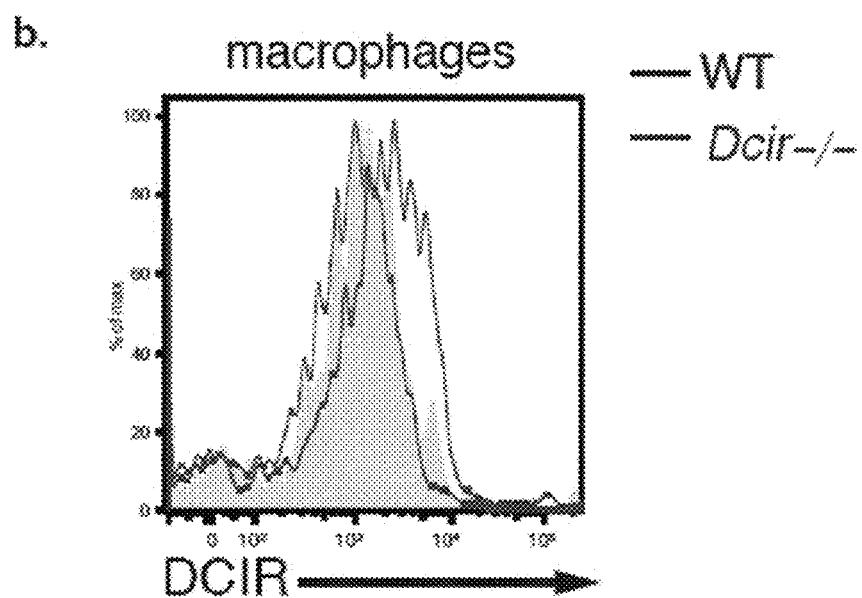
FIG. 3 shows the results of flow cytometric analysis of the DCIR expression at the cell surface of BMMs at day 4 culture. The line with a right-side peak indicates wild-type and the line with a left-side peak indicates Dcir−/−. The gray area indicates an isotype control. The data are representative of at least three independent experiments.
Figure 4:
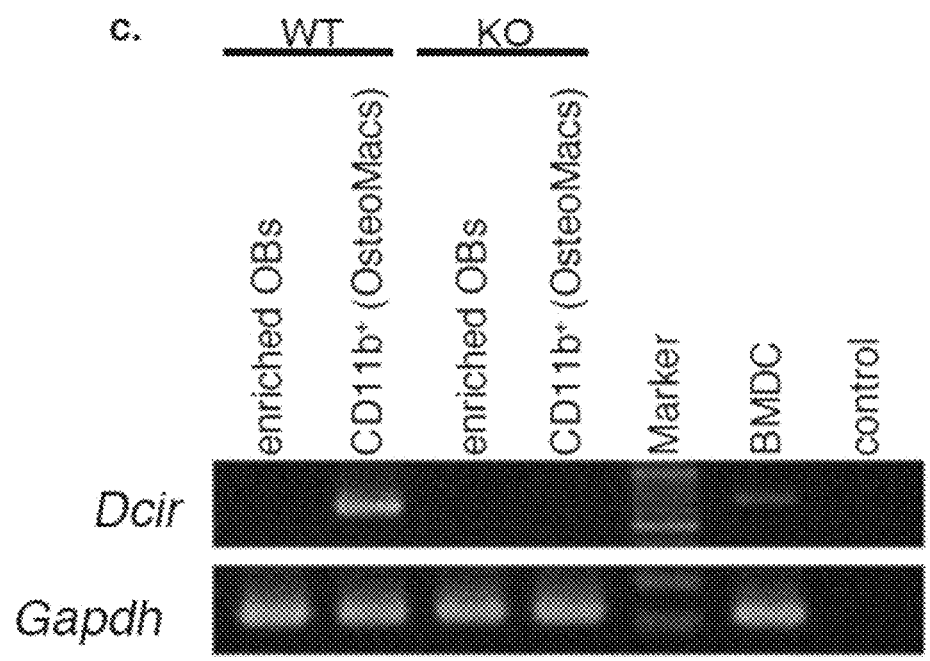
FIG. 4 shows the results of conventional PCR assay in enriched osteoblasts from which CD11b-positive cells were depleted and in CD11b-positive cells (OsteoMacs), where the DCIR expression was not observed in the enriched osteoblasts. The data are representative of three independent experiments.

A DCIR was expressed in M-CSF-induced bone marrow macrophage cells (BMMs) and osteoclasts formed in the presence of M-CSF (macrophage colony-stimulating factor) and RANKL (receptor activator of nuclear factor kappa-B ligand), factors relating to osteoclast differentiation, at mRNA and protein levels (FIGS. 1 to 3). The gene expression progressively increased as the osteoclasts matured. A DCIR was detected in CD11b-positive cells (OsteoMacs) but not in enriched osteoblasts (FIG. 4).

Figure 5:
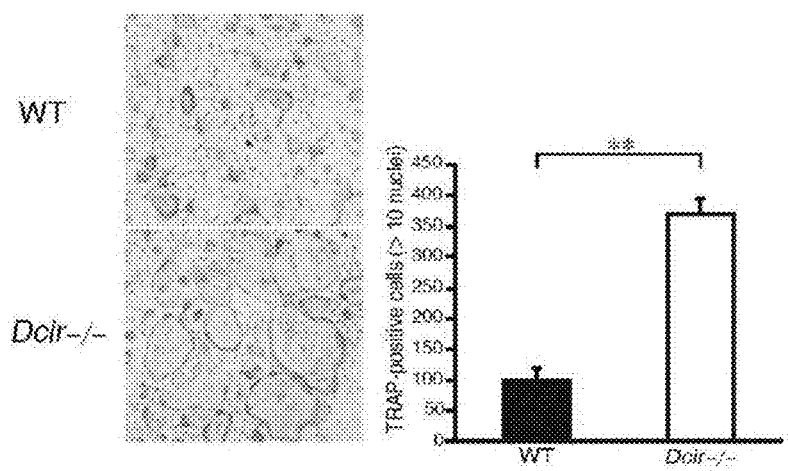
FIG. 5 shows the degree of osteoclast formation in wild-type and Dcir−/− BMMs (10-fold magnification). The data are representative of at least three independent experiments. The error bars present the means±s.d. of triplicate cultures. *P<0.05; **P<0.01.
Figure 6:
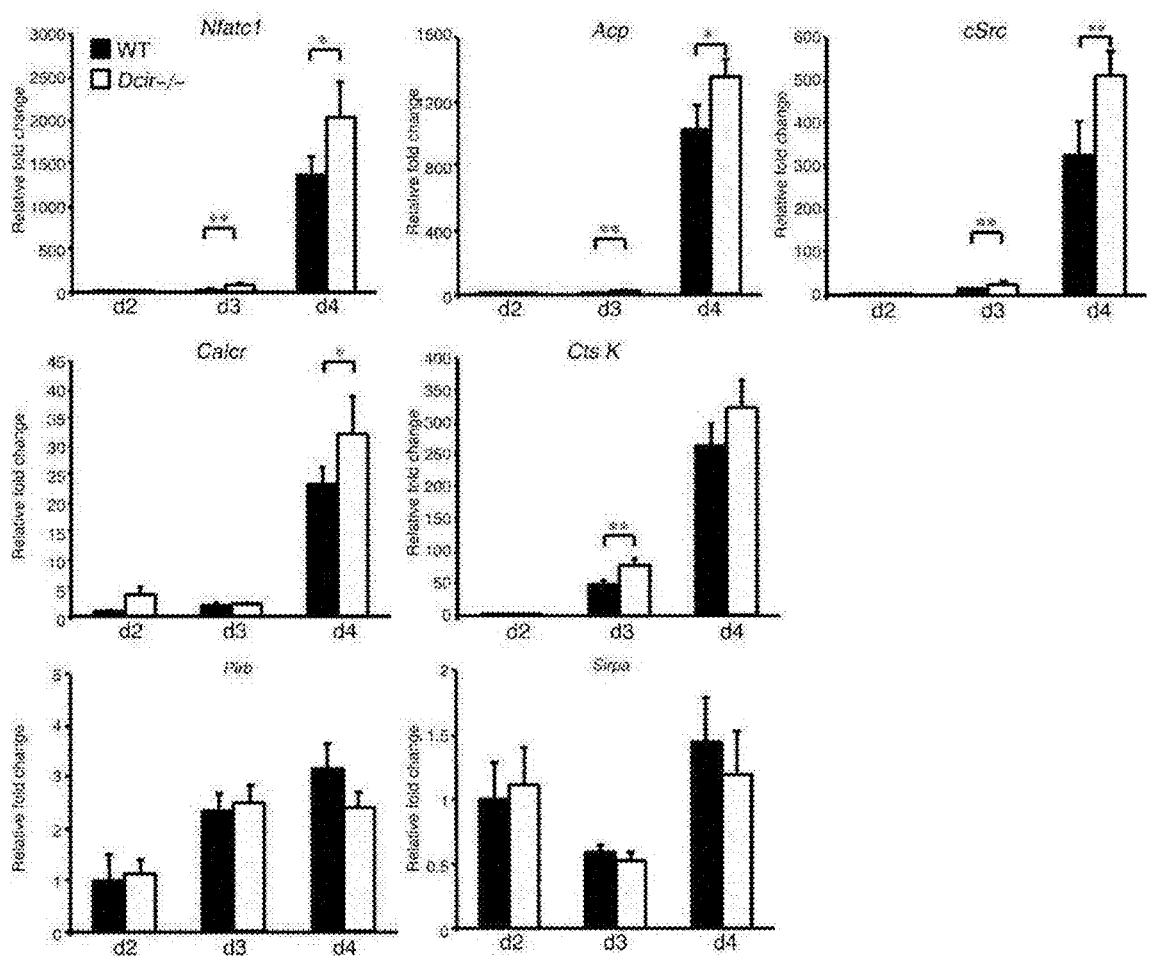
FIG. 6 shows the quantitative data of mRNA of osteoclasts. The results are representative of two or three independent experiments. The error bars represent the means±s.d. of triplicate cultures. *P<0.05; **P<0.01.
Figure 7:
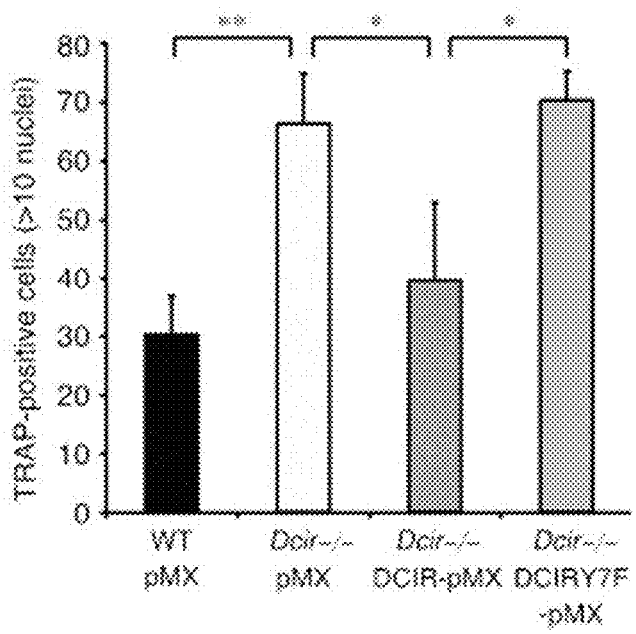
FIG. 7 shows the ITIM-mediated inhibition of osteoclast formation, where Dcir−/− bone marrow cells (BMs) were infected either with DCIR-pMX or DCIRY7F-pMX. The results are representative of three independent experiments. The error bars represent the means±s.d. of triplicate cultures. *P<0.05; **P<0.01.
Figure 8:
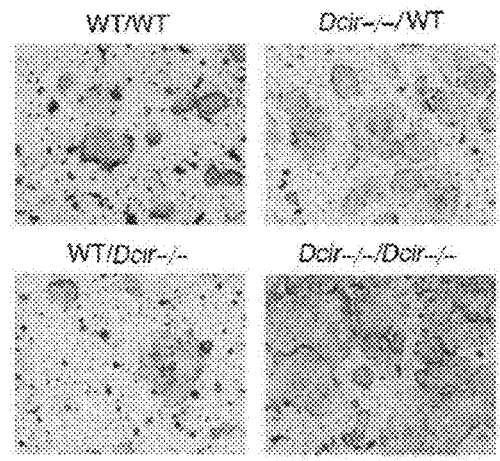
FIG. 8 shows the results of osteoclast formation in co-culture with osteoblasts. The data are representative of at least three independent experiments. The error bars represent the means±s.d. of triplicate cultures. **P<0.01.
Figure 8:
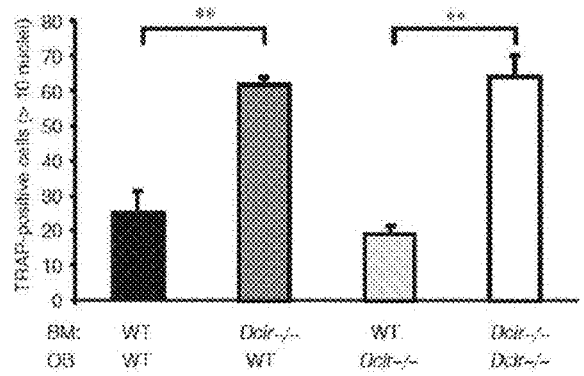
Figure 9:
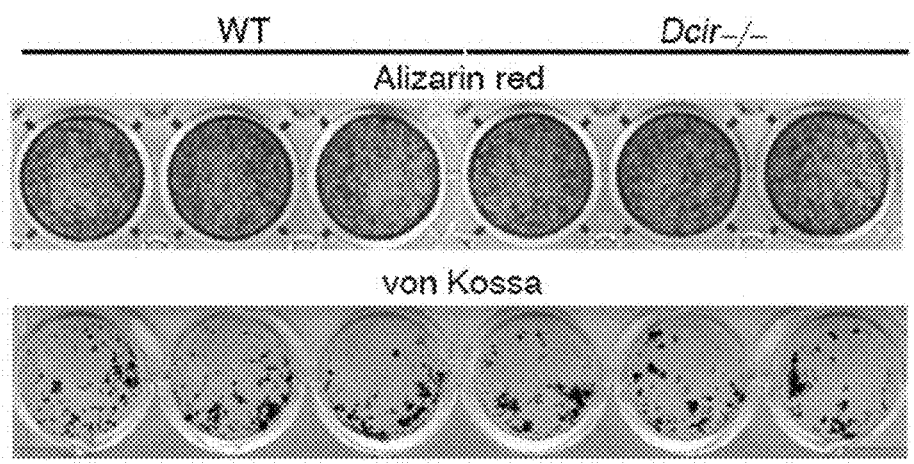
FIG. 9 shows the results of alizarin red and von Kossa stainings of un-sorted primary osteoblasts cultured in osteogenic medium for 14 days. The data are representative of at least three independent experiments.
Figure 10:
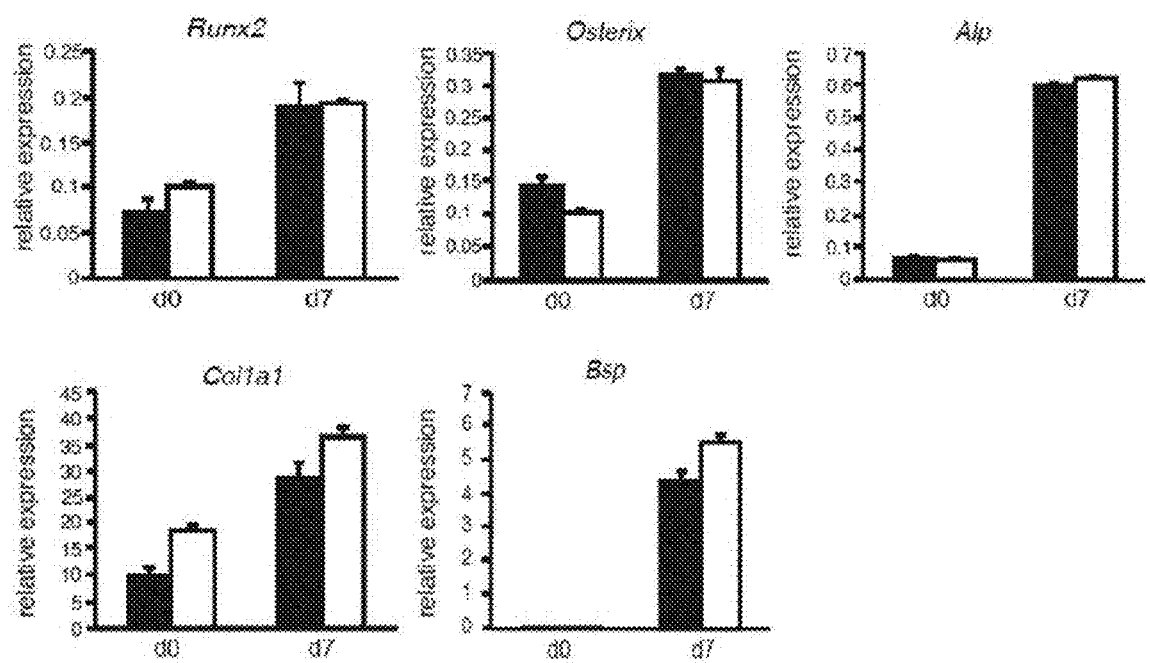
FIG. 10 shows the quantitative data of gene expression of un-enriched osteoblasts at day 0 and day 7 of the culture in osteogenic medium. The data are representative of at least three independent experiments. Error bars represent the means±s.d. of triplicate cultures.
Figure 11:
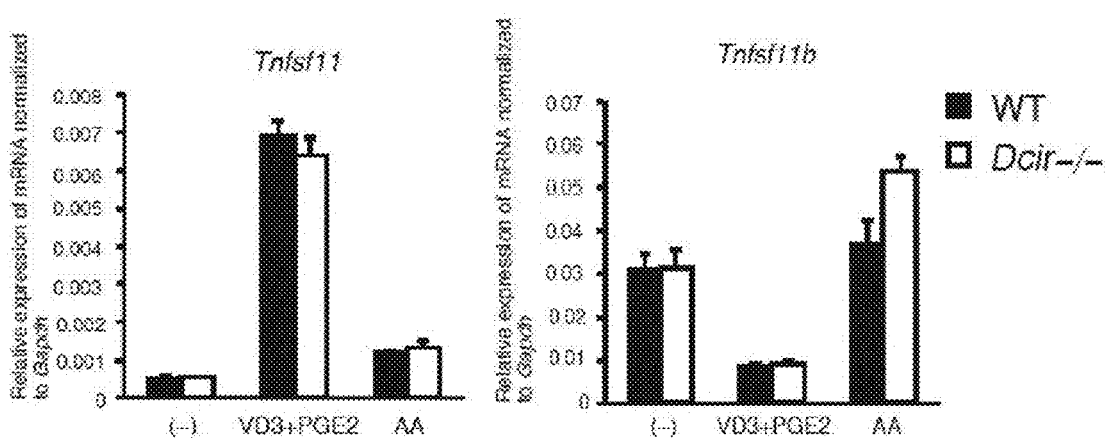
FIG. 11 shows the effect of vitamin D3 (VD3), prostaglandin E2 (PGE2) and ascorbic acid (AA) on osteoblast activation and differentiation. Un-enriched osteoblasts cultured in osteogenic medium were stimulated either with VD3 ($10^{-8}$ M) plus PGE2 ($10^{-6}$ M) or with AA (50 μg/ml) for 24 hours. Gene expression of Tnfsf11 (RANKL) and Tnfsf11b (OPG) was determined by real-time PCR. The error bars represent the means±s.d. of triplicate cultures. The data are representative of at least three independent experiments.

To examine the role of a DCIR in osteoclast formation, we compared the osteoclast formation of Dcir−/− (Dcir deficient) BMMs with that of wild-type BMMs in the presence of M-CSF and RANKL. As a result, formation of osteoclasts was significantly induced in Dcir−/− BMMs with more than ten nuclei positive for tartrate-resistant acid phosphatase (TRAP), a marker of osteoclasts (FIG. 5). The expression of osteoclastic genes significantly increased in Dcir−/− osteoclasts, but ITIM-harboring receptors were unchanged (FIG. 6). The pronounced osteoclast differentiation was efficiently reduced by the retroviral expression of a DCIR, but not by a mutant DCIR (DCIRY7F) that lacked the ability to deliver inhibition signaling, indicating that ITIM-mediated signaling is required for the DCIR-induced suppression of osteoclast formation (FIG. 7). Notably, the osteoclast formation of Dcir−/− BMMs was promoted in the co-culture system of non-adherent bone marrow cells with osteoblasts, proving that a DCIR non-redundantly downregulates osteoclast formation (FIG. 8). There was no difference in the osteoblast differentiation between the wild-type and Dcir−/− mice (FIGS. 9 to 11).

From these results, it is confirmed that the DCIR-mediated signaling negatively regulates formation of osteoclasts, and that the DCIR deficiency promotes formation of osteoclasts.

Experiment 2

Figure 12:
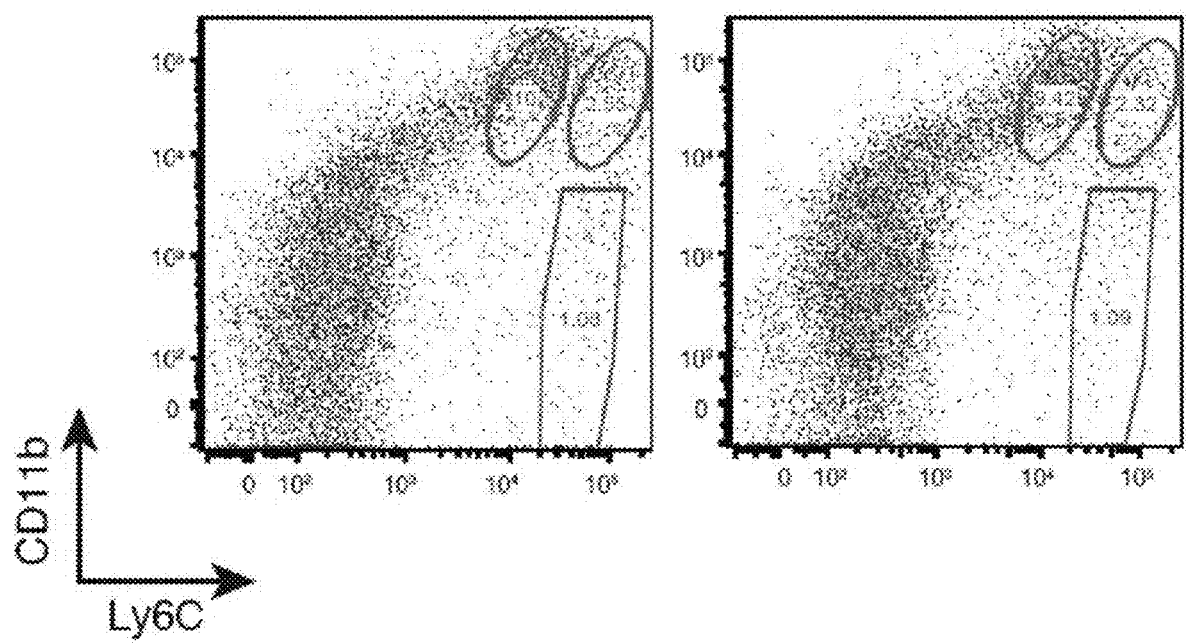
FIG. 12 shows the result of flow cytometric analysis of osteoclast precursor population in 8-week-old wild-type and Dcir−/− mice. Bone marrow cells gated as a negative for CD3, B220 and Ter119 were plotted against CD11b and Ly6C. Each plot represents the data of three mice. The data are representative of two independent experiments.
Figure 13:
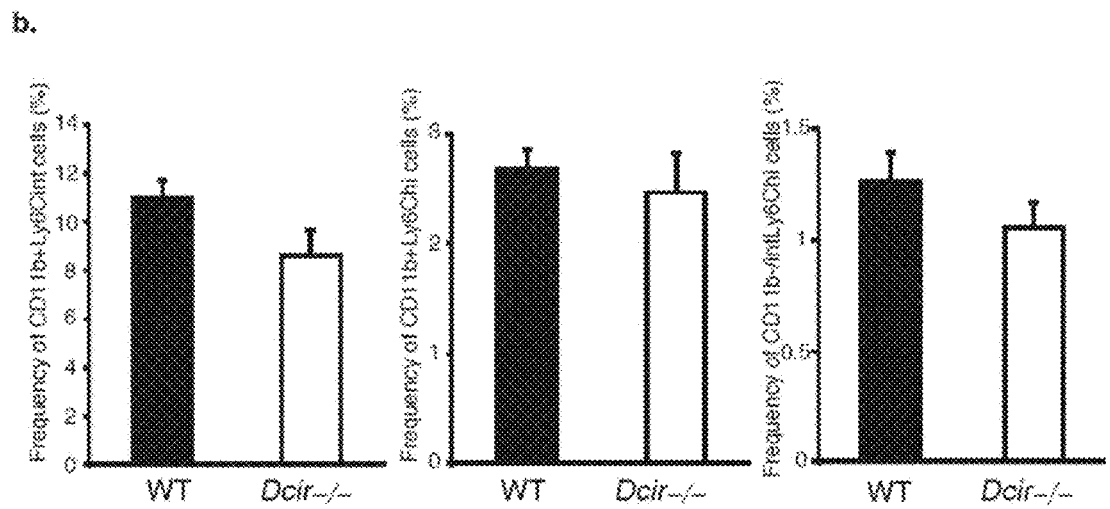
FIG. 13 shows the frequency of osteoclast precursor population characterized by $CD11b^{lo}Ly6C^{hi}$. Data present the means±s.d. of three mice. The data are representative of two independent experiments.

To confirm the frequency of osteoclast precursor populations in bone marrow, we examined hematopoietic cell populations in bone marrow. A flow cytometric analysis showed that the frequency of osteoclast precursors in the Dcir−/− mice, identified as CD11b$^{lo}$Ly6C$^{hi}$, was comparable with that of the wild-type mice (FIGS. 12 and 13), demonstrating that DCIR is implicated in the process of osteoclast differentiation.

Figure 14:
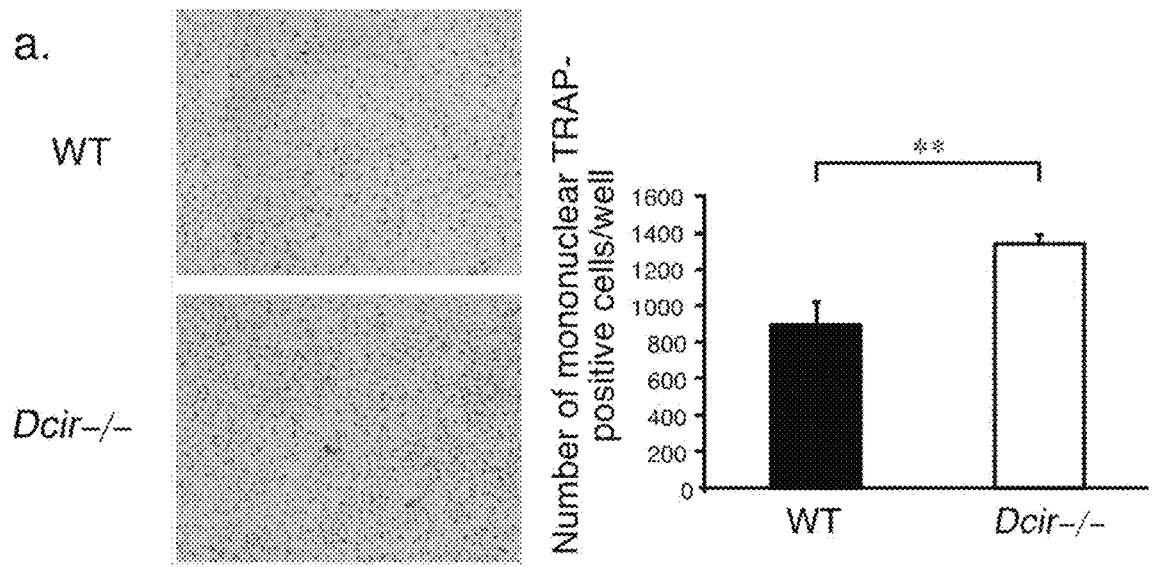
FIG. 14 is a graph showing the increase in the number of TRAP-positive mononuclear cells (MNCs) of Dcir–/– mice immediately before the appearance of osteoclast fusion (4-fold magnification). The result is representative of at least three independent experiments. The error bars represent the means±s.d. of triplicate cultures. **$P<0.01$.
Figure 15:
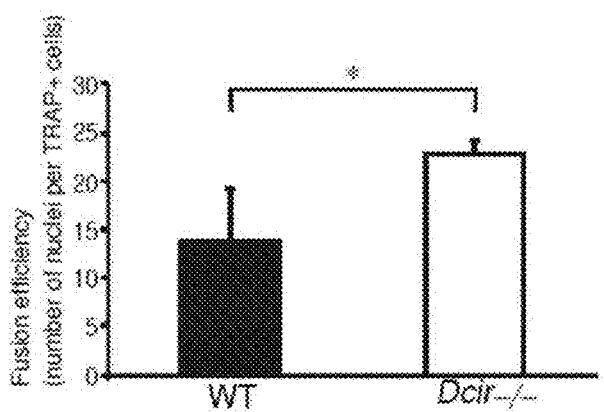
FIG. 15 shows the result of inducing osteoclast formation of wild-type BMMS and Dcir–/– BMMs of the same number in the presence of M-CSF and RANKL and performing TRAP staining and haematoxylin staining, represented as the fusion efficiency (number of nuclei/number of TRAP positive cells). The data are representative of two independent experiments. The error bars represent the means±s.d. of triplicate cultures. **$P<0.05$.

It appears that an increase in the number of mononuclear cells (MNCs) result in an increase in osteoclast formation due to the DCIR deficiency. To test this hypothesis, we counted TRAP-positive wild-type and Dcir−/− MNCs before the multinucleated osteoclasts appeared, and observed a considerable number of TRAP-positive Dcir−/− MNCs, relative to wild-type MNCs (FIG. 14). Moreover, we examined whether or not the DCIR deficiency affected the cell-cell fusion of MNCs, a characteristic of osteoclasts. As a result, a significantly larger number of nuclei in TRAP-positive cells were observed in Dcir−/− MNCs, after an equal number of BMMs were re-plated to induce differentiation by RANKL (FIG. 15). In addition, increased responsibility with respect to RANKL is considered to be a reason for the increased osteoclast formation. The result of quantification of expression of genes specifically induced by RANKL stimulus (Nfatc1, Acp, cSrc, Calcr and CtsK) shows the increased expression in Dcir−/− osteoclasts (FIG. 16).

Figure 16:
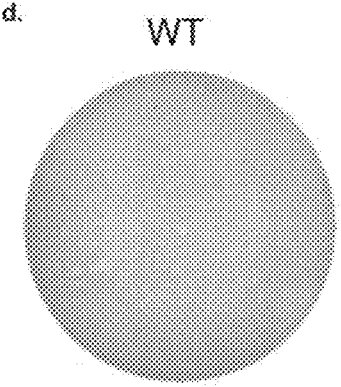
FIG. 16 is an image after re-seeding the wild-type osteoclasts and Dcir–/– osteoclasts of the same number, formed in the presence of M-CSF and RANKL, in an Osteo Assay plate and culturing for further 5 days in the presence of M-CSF and RANKL (4-fold magnification), and the result of analysis with ImageJ of the area resorbed by the osteoclasts. The data are representative of two independent experiments. The error bars present the means±s.d. of triplicate cultures. **$P<0.01$.
Figure 16:
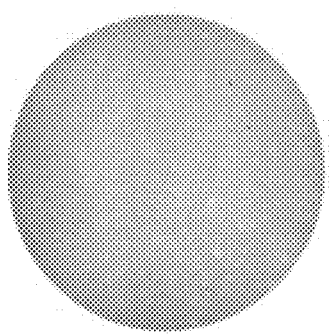
Figure 16:
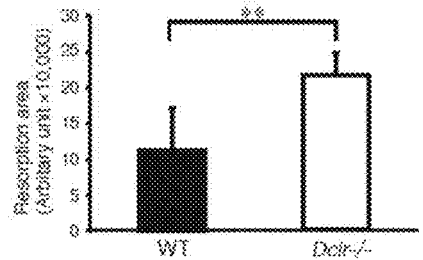
Figure 16:
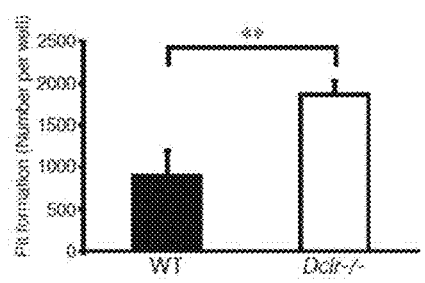
Figure 17:
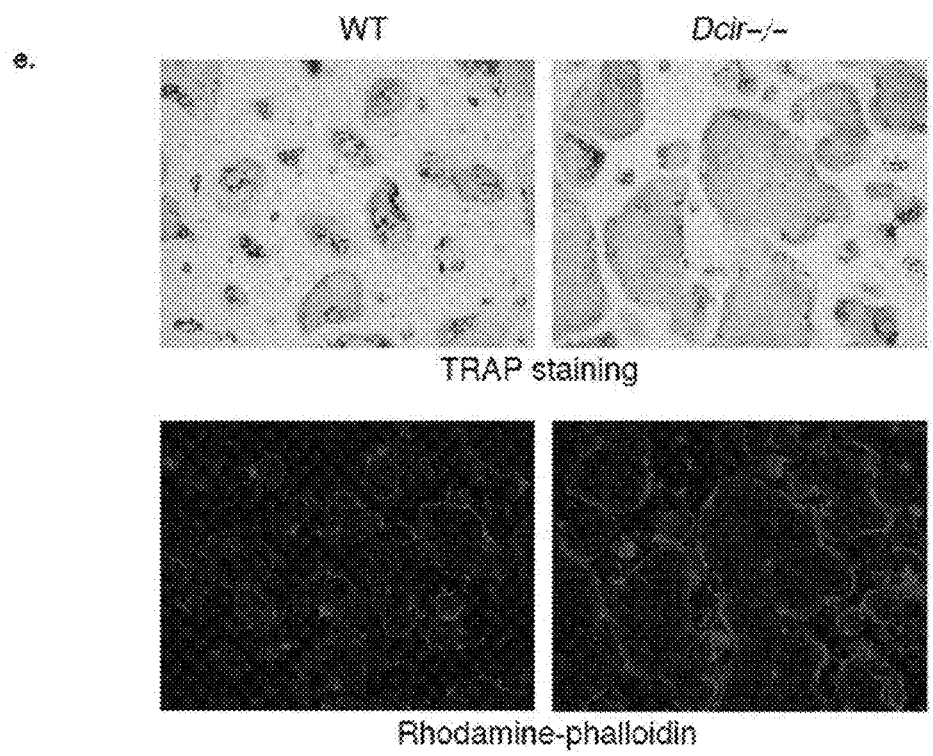
FIG. 17 shows the result of osteoclast formation by TRAP staining and actin cytoskeleton formation by rhodamine-phalloidin staining. The data are representative of two independent experiments.

In addition, the DCIR deficiency results in an increase in the size of the resorption area and the number of pits, which is consistent with significant osteoclast formation (FIG. 16). In contrast, the DCIR deficiency had no effect on the formation of the actin ring, a prerequisite structure for osteoclast resorption (FIG. 17). Thus, it is confirmed that a DCIR is an important negative regulator in osteoclast formation.

Figure 18:
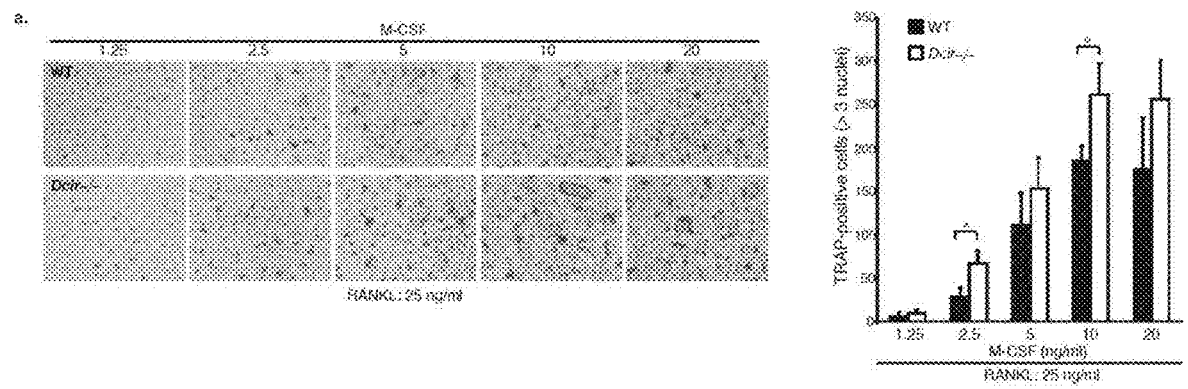
FIG. 18 is an image of non-adherent BM cells from wild-type and Dcir–/– mice cultured in the presence of the indicated concentrations of M-CSF and 25 ng/ml of RANKL (4-fold magnification). TRAP staining was performed after 5 days of the culture, and the multinucleated osteoclasts with more than three nuclei were counted. The data are representative of two independent experiments. The error bars represent the means±s.d. of triplicate cultures. **$P<0.01$.
Figure 19:
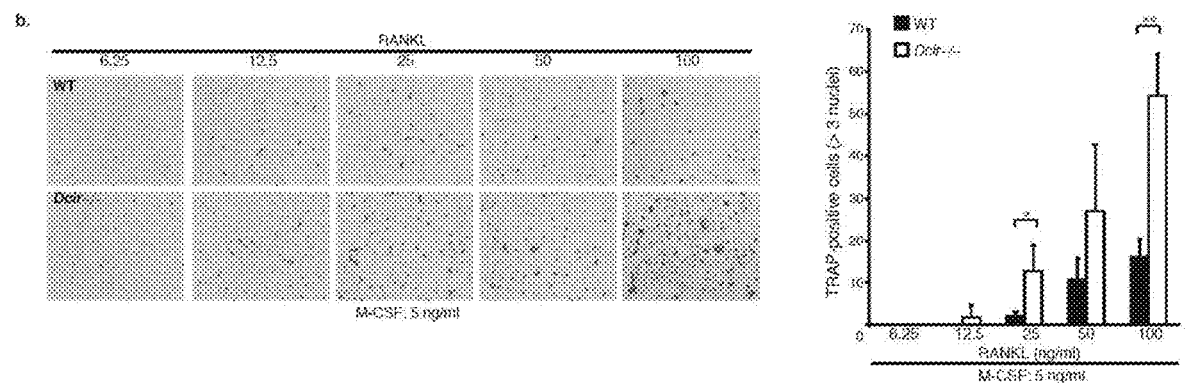
FIG. 19 is an image of non-adherent BM cells from wild-type and Dcir–/– mice cultured in the presence of the various concentrations of RANKL and 5 ng/ml of M-CSF (4-fold magnification). TRAP staining was performed after 5 days of the culture, and the multinucleated osteoclasts with more than three nuclei were counted. The data are representative of two independent experiments. The error bars represent the means±s.d. of triplicate cultures. *$P<0.05$; **$P<0.01$.
Figure 20:
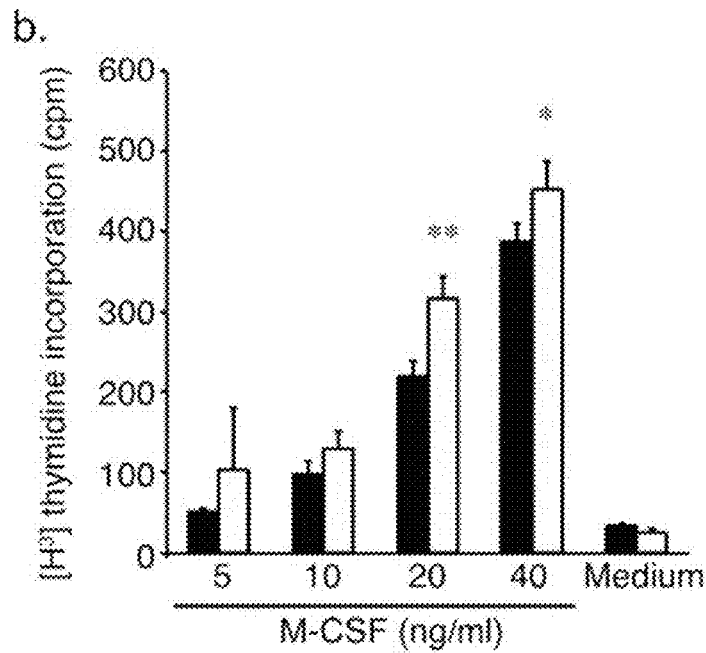
FIG. 20 is a graph showing that the BMMs proliferate in response to M-CSF. The data are representative of three independent experiments. The error bars present the means±s.d. of triplicate cultures. *$P<0.05$; **$P<0.01$.

It has been reported that the increased osteoclast differentiation, in an in vitro assay of osteoclast formation with M-CSF and RANKL, may result from high sensitivity to these factors. To ascertain whether this is actually the case, the concentration of one factor was progressively increased, while that of the other was left constant. As a result, in all cultures, the concentration of the constant cytokine was smaller than that used in our normal culture system. In response to M-CSF and RANKL, while the number of TRAP-positive multinucleated Dcir−/− cells tended to rise, no such rise was observed in wild-type cells (FIGS. 18 and 19), suggesting that the DCIR deficiency may render BMMs to be hyperresponsive to M-CSF and RANKL. Consistent with this hyperresponsivness to M-CSF, the Dcir−/− BMMs exhibited a higher proliferation in response to M-CSF (FIG. 20).

Figure 21:
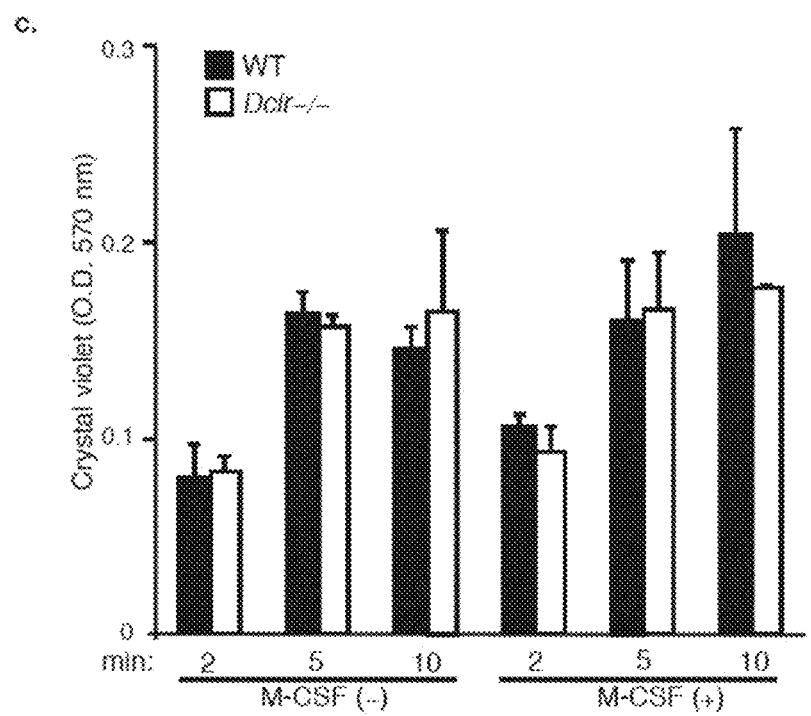
FIG. 21 is a graph showing the absorbance measured at 570 nm on the equal number of wild-type and Dcir–/– BMMs placed on plates coated with fibronectin and incubated for 2, 5 and 10 minutes with or without M-CSF. Adherent cells were stained with crystal violet (0.5%). The data are representative of two independent experiments. The error bars represent the means±s.d. of triplicate cultures.
Figure 22:
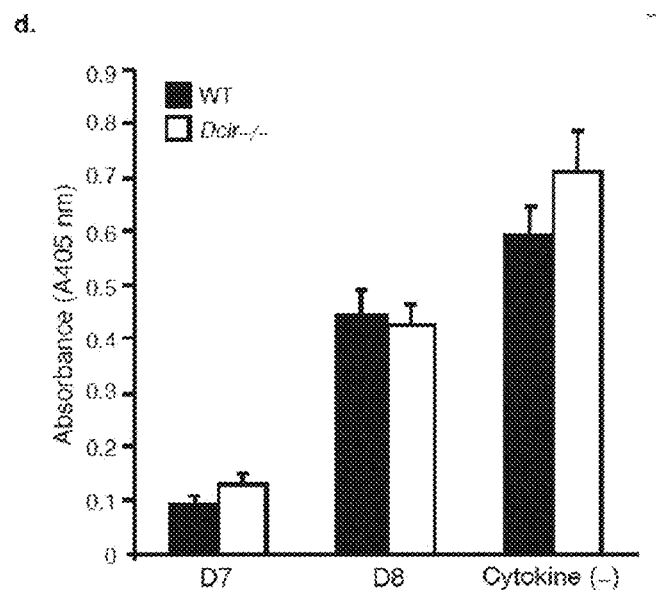
FIG. 22 is a graph showing the result of detection by ELISA of mono- and oligonucleosomes in the cytoplasmic fraction of cell lysates. The equal number of wild-type and Dcir–/– BMMs were induced to form osteoclasts for 7 and 8 days. M-CSF and RANKL removal from the osteoclast culture at 8 days for 6 hours was used as a positive control of apoptosis. The data are representative of two independent experiments. The error bars represent the means±s.d. of triplicate cultures.
Figure 23:
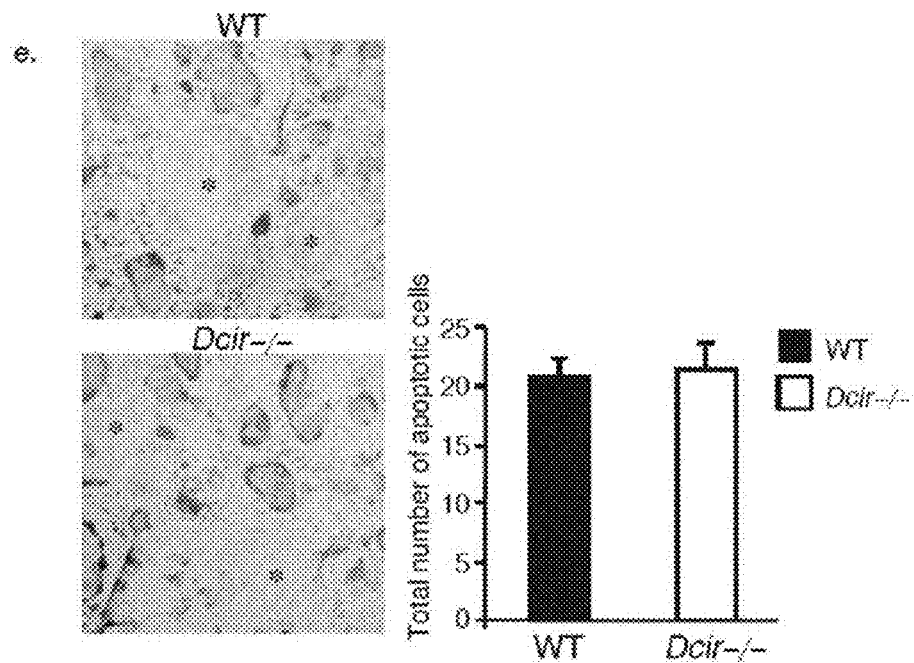
FIG. 23 shows TRAP-positive cells visualized (4-fold magnification) in osteoclasts induced from the equal number of BMMs from wild-type and Dcir–/– mice. Apoptotic or dead cells are indicated by asterisks. The graph shows the number of apoptonic cells. The data are representative of two independent experiments. The error bars represent the means±s.d. of triplicate cultures.

Although M-CSF is known to be involved in macrophage adhesion and osteoclast survival, the adhesive activity of Dcir−/− BMMs and apoptosis of long-term cultured Dcir−/− osteoclasts were unaltered (FIGS. 21 to 23), indicating that the DCIR-mediated signaling downregulates the proliferation induced by M-CSF.

Figure 24:
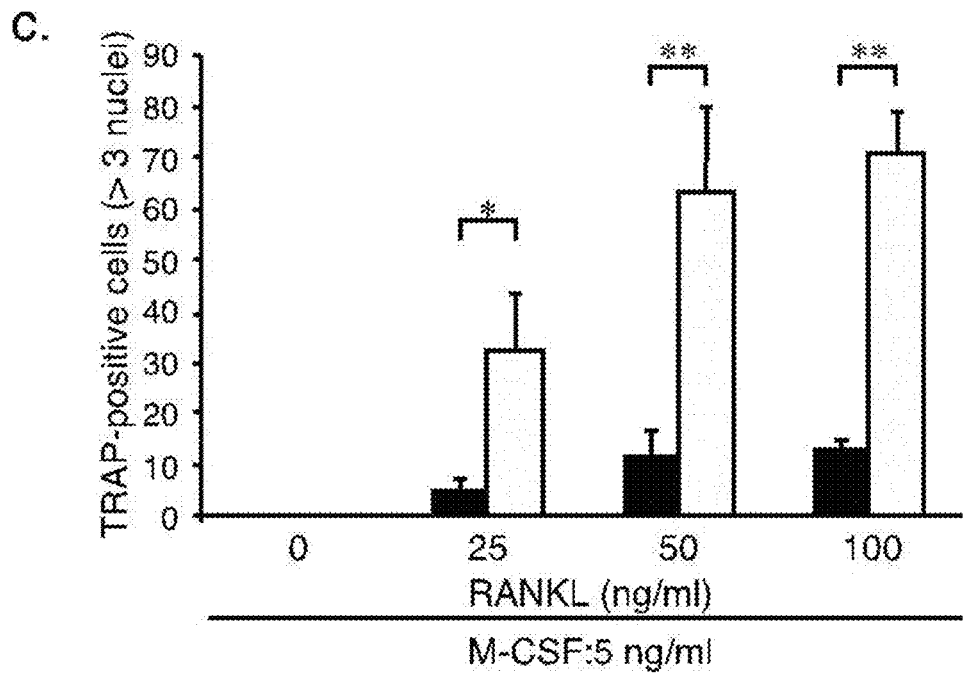
FIG. 24 shows that the equal number of BMMs from wild-type and Dcir–/– mice were induced to osteoclasts at various concentrations of RANKL and 5 ng/ml of M-CSF. Data are representative of three independent experiments. The error bars represent the means±s.d. of triplicate cultures. *$P<0.05$; **$P<0.01$.
Figure 25:
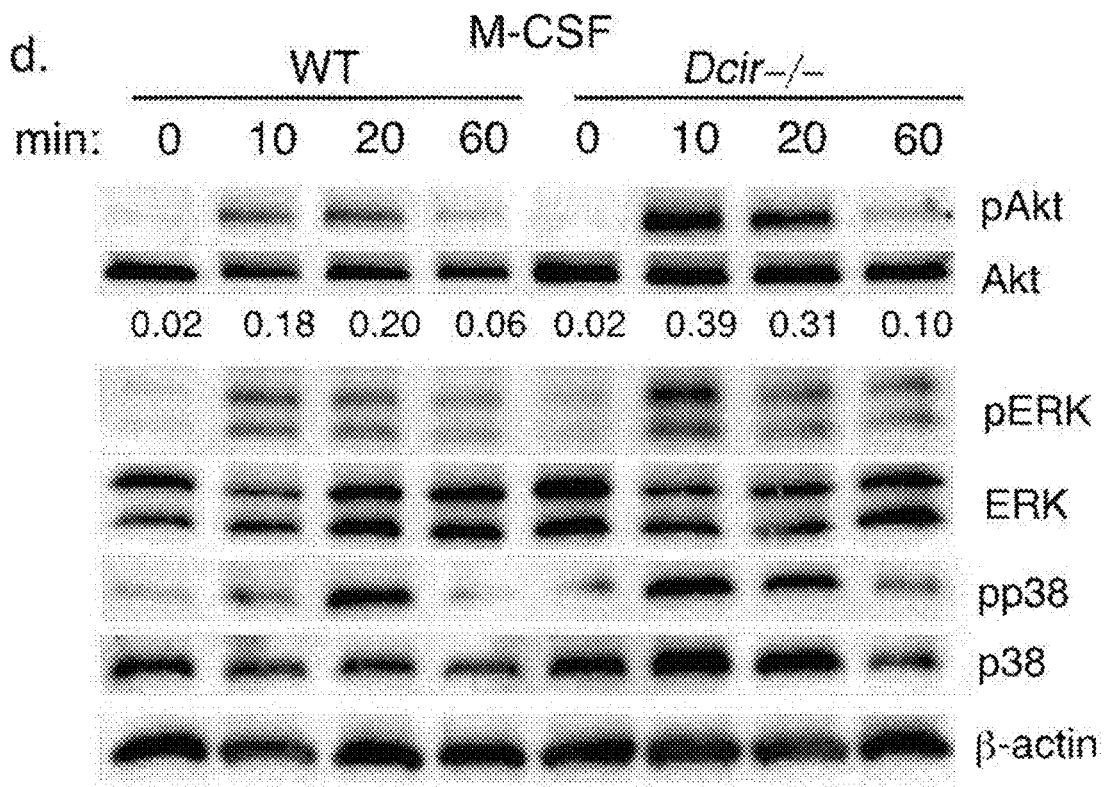
FIG. 25 shows that the Akt signal in Dcir–/– BMMs in response to M-CSF and RANKL is enhanced. The value below each lane presents the relative signal density of phosphorylated kinase normalized to loaded kinase. The data are representative of at least three independent experiments.
Figure 25:
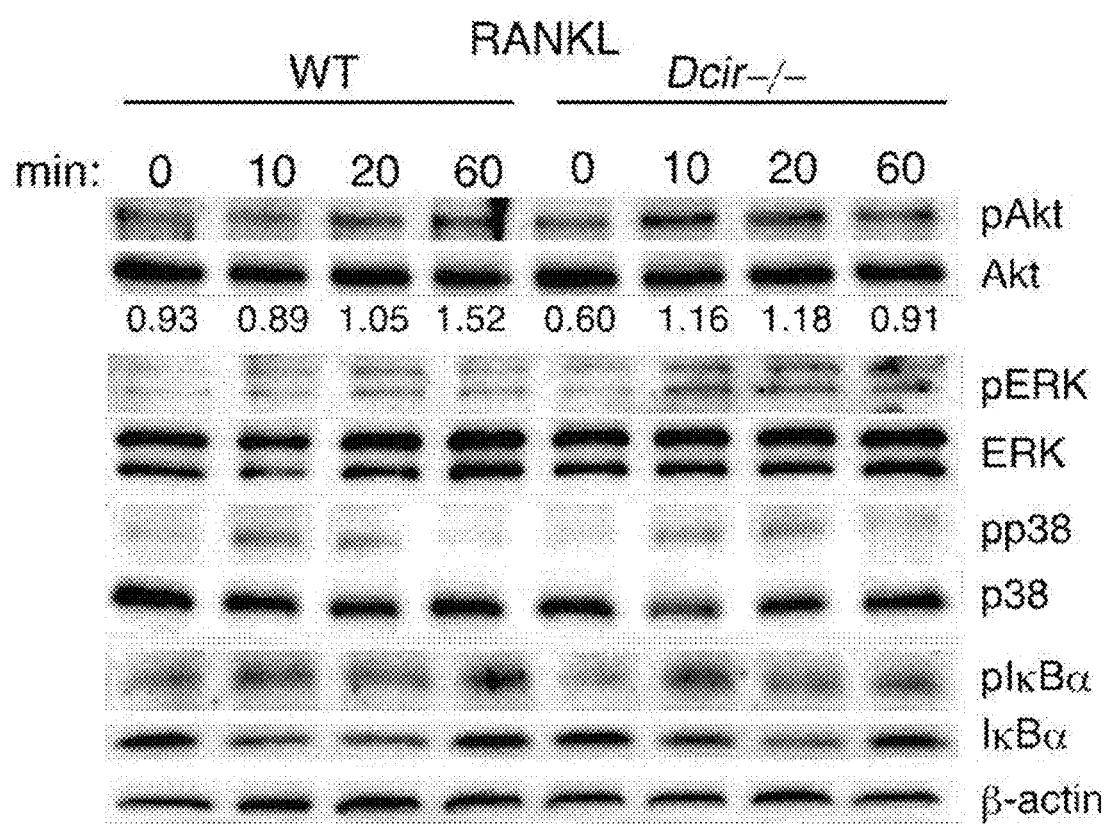

In addition, when osteoclasts were grown from an equal number of BMMs at the beginning of the culture, Dcir−/− BMMs were clearly differentiated to multinucleated osteoclasts even in low concentrations of RANKL (FIG. 24), indicating that the enhanced osteoclast formation in Dcir−/− BMMs is caused by a coordinated effect of increased proliferation in response to M-CSF and elicited differentiation in response to RANKL. To gain insight into the molecular basis of the defective DCIR-mediated increase in osteoclast formation, we analyzed the phosphorylation levels of the signaling components downstream from c-Fms, a tyrosine kinase receptor for M-CSF, and RANK, a receptor for RANKL. As a result, M-CSF and RANKL induced more phosphorylation of Akt in Dcir−/− BMMs, but the activation of ERK, p38, and IκBα was comparable (FIG. 25). These data indicate that the activation of the Akt signaling pathway upon M-CSF and RANKL stimuli enhances osteoclast formation.

From these results, it is confirmed that the DCIR deficiency enhances responsibility of BMMs to M-CSF and RANKL.

Experiment 3

Figure 26:
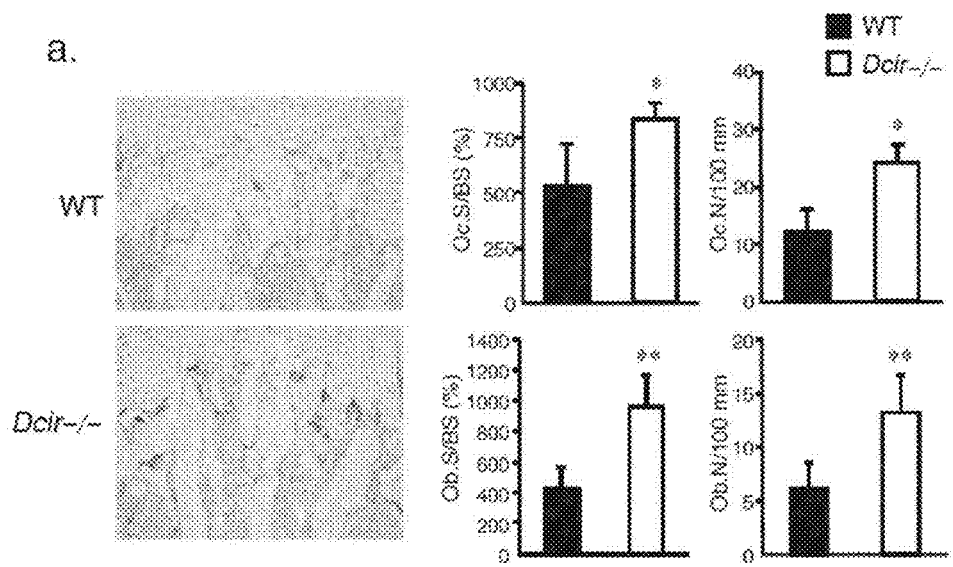
FIG. 26 shows the result of histological analysis of tibia in 8-week-old wild-type and Dcir–/– mice. The error bars represent the means±s.e.m (n=4 to 6) *$P<0.05$; **$P<0.01$.
Figure 27:
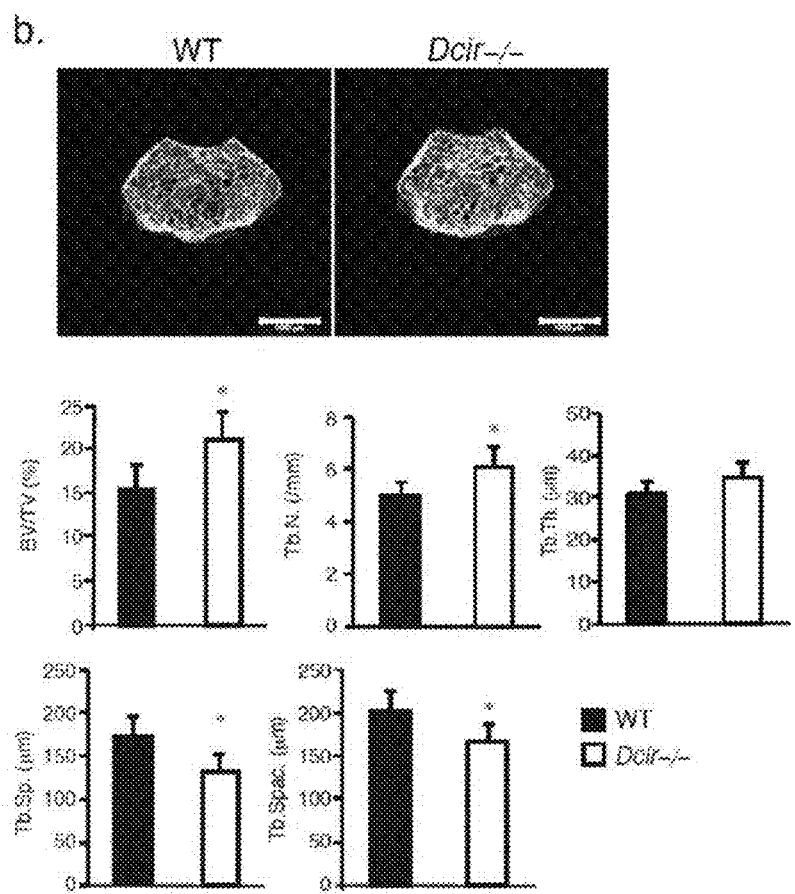
FIG. 27 shows microcomputed tomography images and bone parameters of femoral trabeculae in 8-week-old wild-type and Dcir–/– mice. The data are representative of two independent experiments. The error bars represent the means±s.e.m (n=4 to 6) *$P<0.05$.
Figure 28:
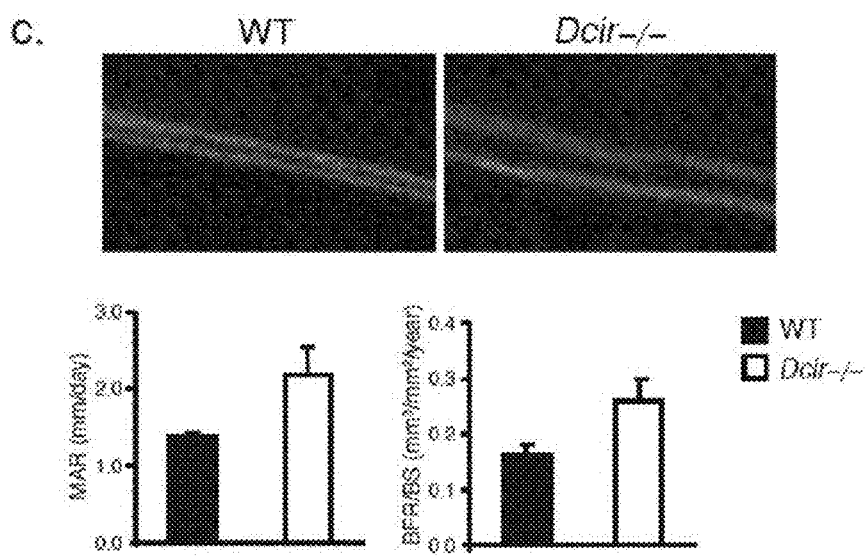
FIG. 28 shows in vivo bone formation in 8-week-old wild-type and Dcir–/– mice by calcein double labeling. The data are representative of two independent experiments. The error bars represent the means±s.e.m (n=4 to 6).

Further investigation into the bone architecture of Dcir−/− mice was carried out by means of a histomorphometric analysis of the tibia distal metaphysis, which revealed an increase in both the osteoclastic and osteoblastic parameters (FIG. 26). A microcomputed tomography showed that Dcir−/− mice at 8 weeks of age had mild osteopetrosis in the femurs (FIG. 27), with increases in the bone volume and trabecular number (FIG. 27). Further, a dynamic histomorphometric analysis indicated a higher mineral apposition rate and bone formation rate per unit of trabecular bone surface in Dcir−/− mice (FIG. 28). These results suggest that the DCIR deficiency results in a higher turnover of bone microstructure, where bone formation by osteoblasts is dominant over bone destruction by osteoclasts.

Figure 29:
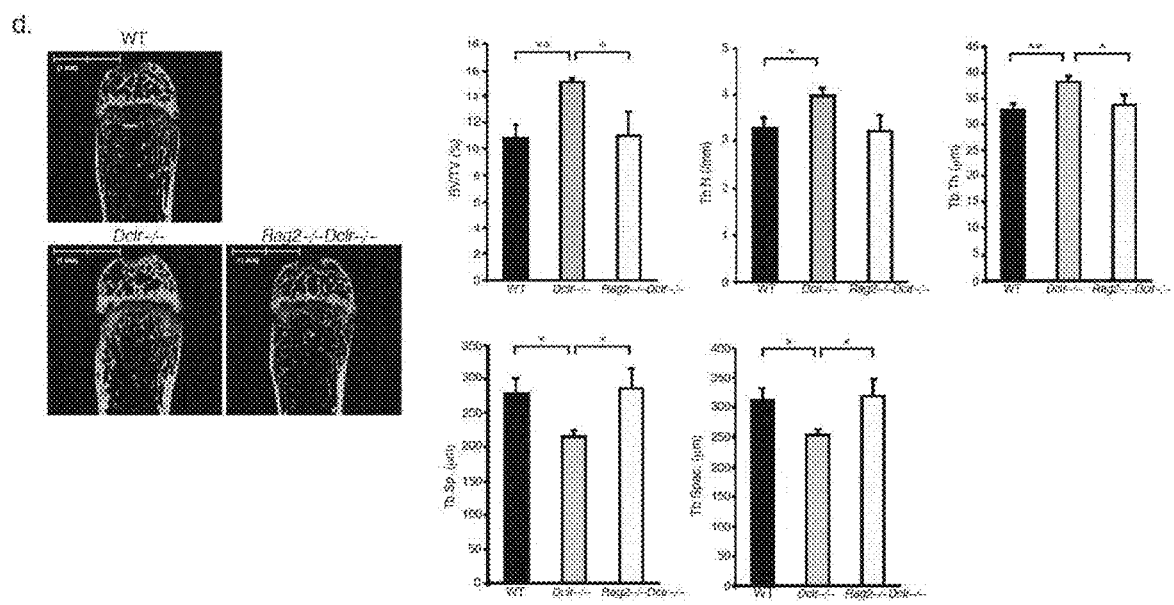
FIG. 29 shows X-ray micro-computed tomographic images and bone parameters of the distal sites of femurs in 9-week-old wild-type, Dcir–/–, and Rag2–/–Dcir–/–mice. The error bars represent the means±s.e.m (n=4 to 6) *$P<0.05$; **$P<0.01$.

The increase in bone volume in Dcir−/− mice appears to contradict our in vitro findings that the DCIR deficiency promotes osteoclast formation but does not affect osteoblast formation. As T cell subsets are involved in regulating osteoclast formation and the DCIR deficiency developed autoimmune-like symptoms because of dysfunctional dendritic cells, our attention turned to the T cell properties in Dcir−/− mice. As a result, the increase of bone volume was cancelled in Rag2−/−Dcir−/− mice (FIG. 29), strongly suggesting that the T cells involve in bone homeostasis.

Figure 30:
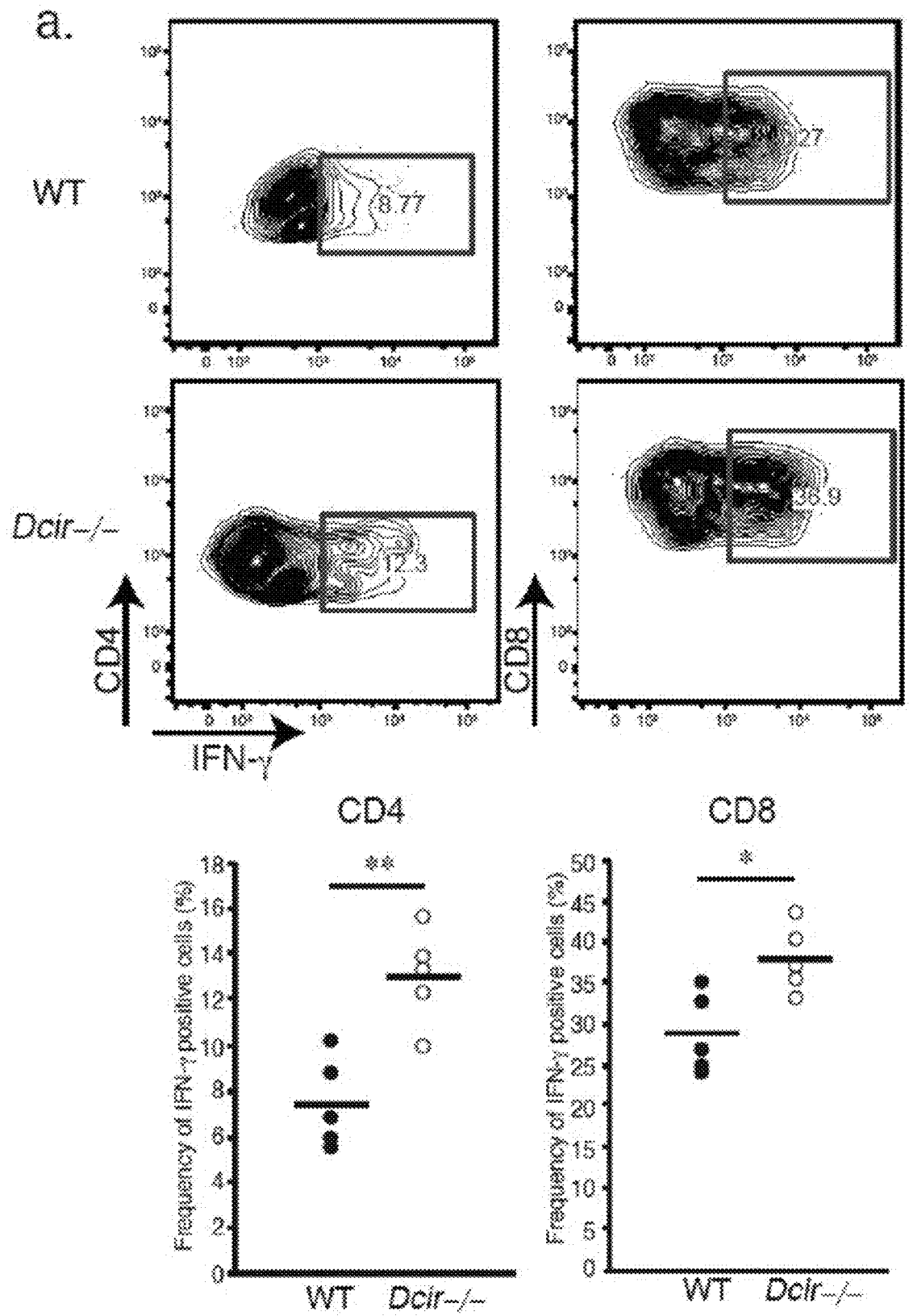
FIG. 30 shows the result of flow cytometric analysis of IFN-γ-positive T cells in peripheral blood. The data are representative of three independent experiments.
Figure 31:
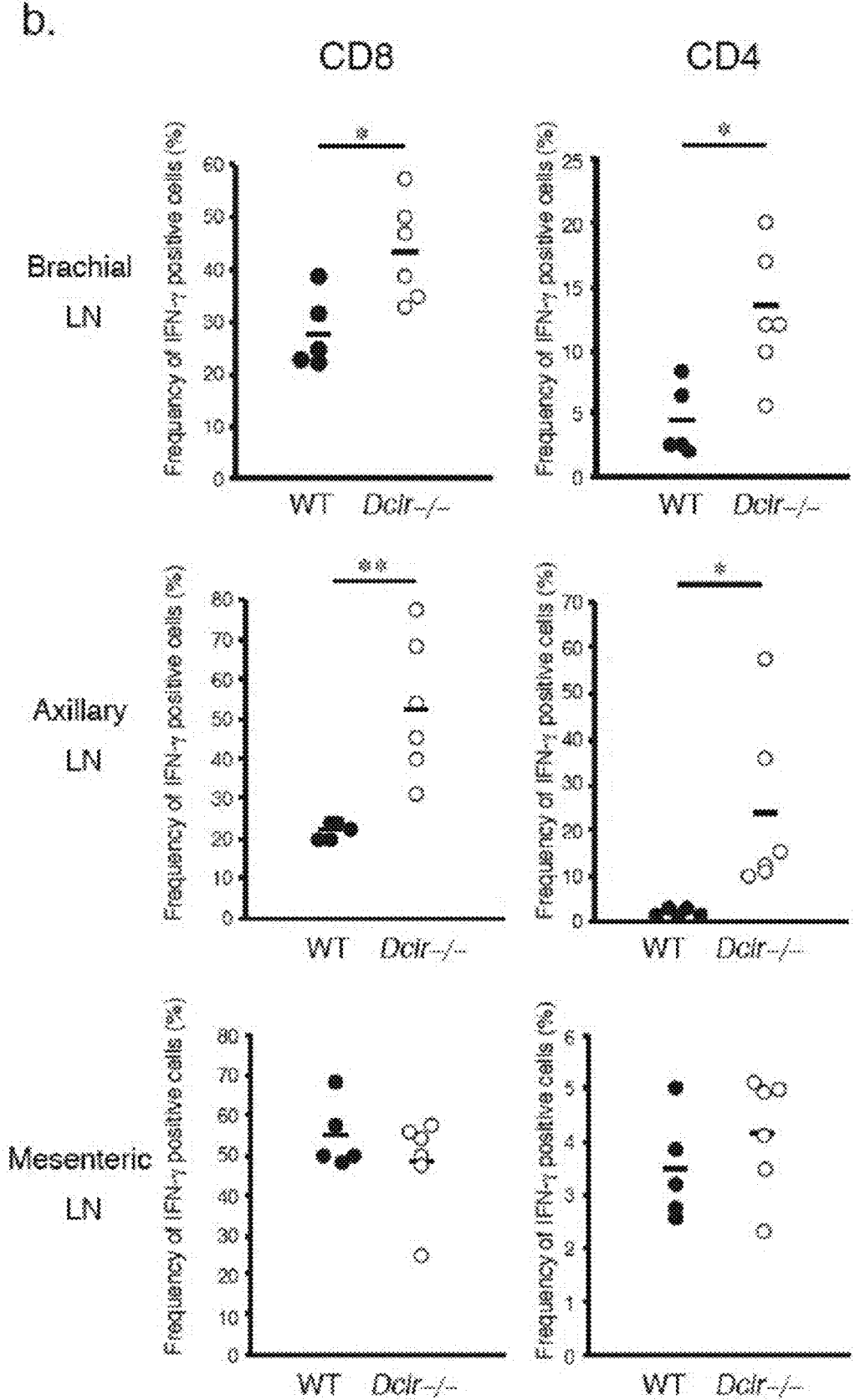
FIG. 31 shows the result of flow cytometric analysis of IFN-γ-positive T cells in lymph nodes. The data are representative of three independent experiments. The error bars represent the means±s.e.m (n=4 to 6) *$P<0.05$; **$P<0.01$.
Figure 32:
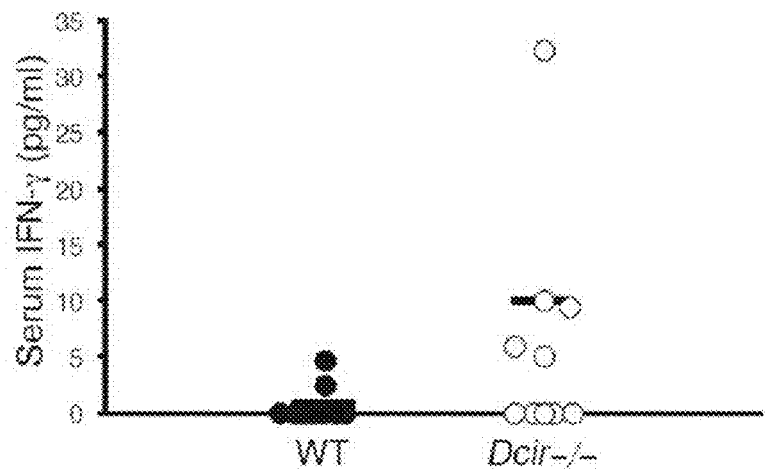
FIG. 32 shows the result of ELISA analysis on the serum concentration of IFN-γ from wild-type (n=10) and Dcir–/– mice (n=10) at an age of 12-week olds. P value between wild-type and Dcir–/– mice is 0.10 in unpaired two-tailed student's t-test. The Data are representative of three independent experiments. Wild-type mice are indicated by black circles and Dcir–/– mice are indicated by white circles. Each symbol is the value of IFN-γ concentration from individual mouse.
Figure 33:
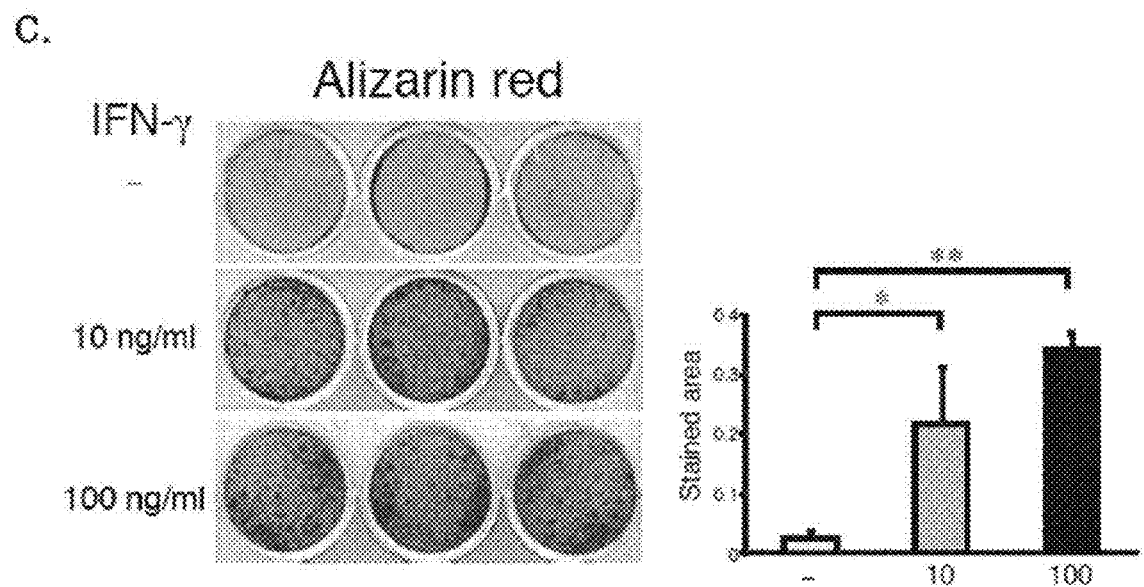
FIG. 33 shows the effect of exogenous addition of IFN-γ on osteoblast formation. The total area of alizarin red staining was analyzed by NIH Image J. The data are representative of at least three independent experiments. The error bars represent the means±s.d. of triplicate cultures, *$P<0.05$, **$P<0.01$.
Figure 34:
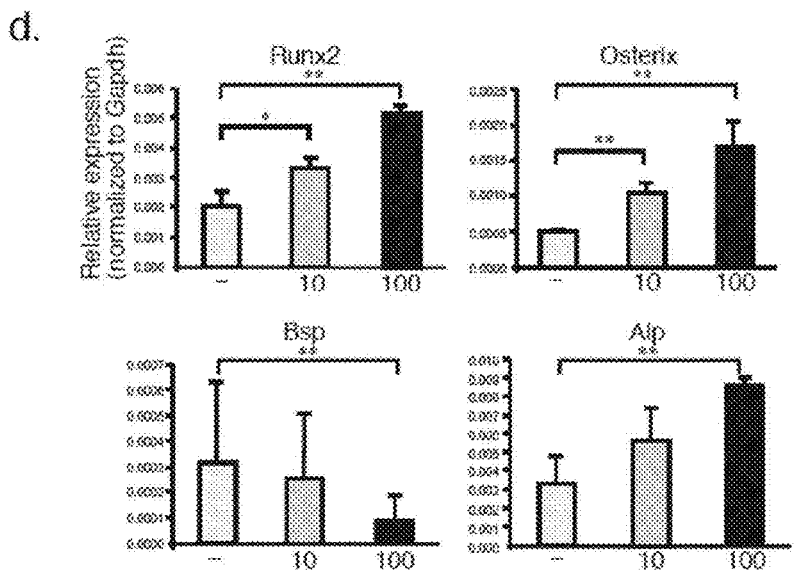
FIG. 34 shows the osteogenic gene expression in the treatment of IFN-γ at day 14 culture. The data are representative of at least three independent experiments. The error bars represent the means±s.d. of triplicate cultures, *$P<0.05$, **$P<0.01$.
Figure 35:
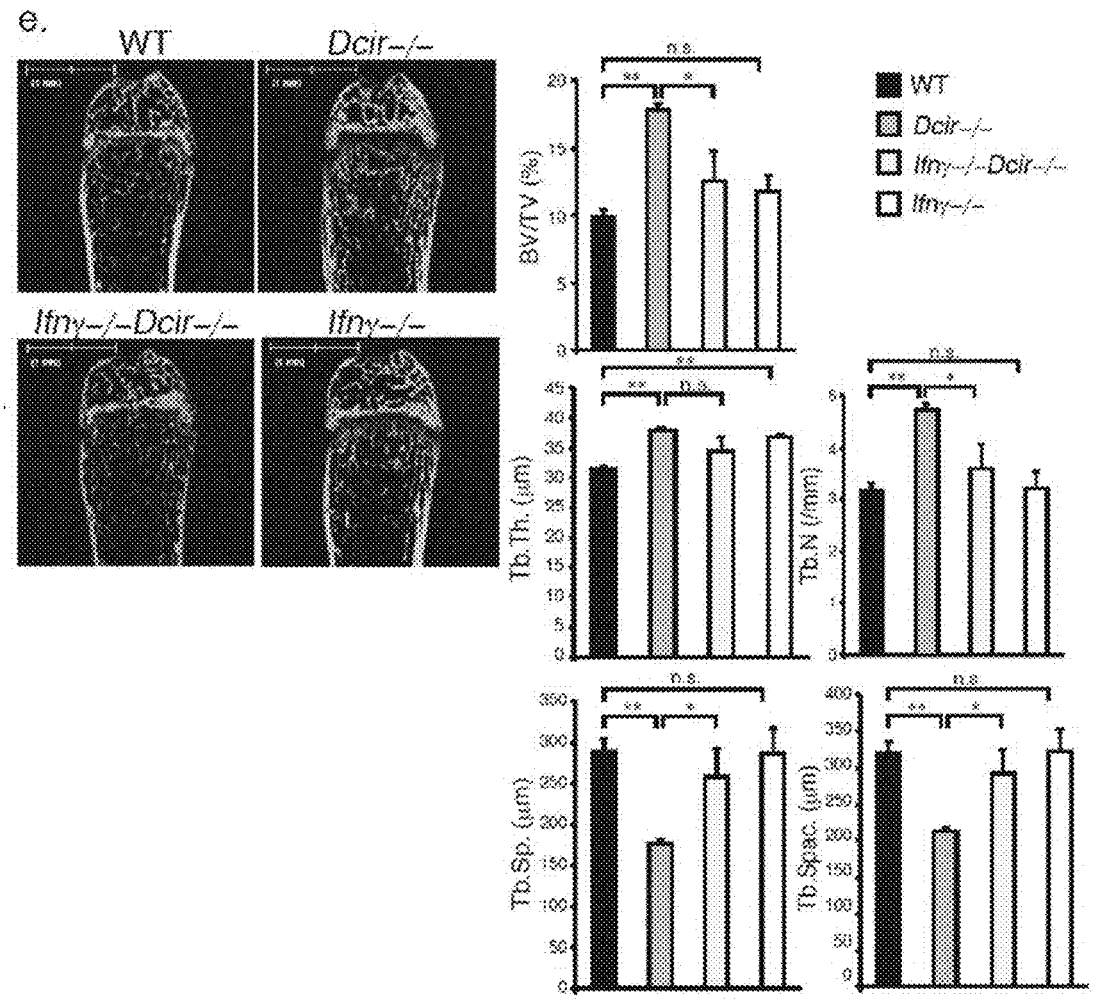
FIG. 35 shows X-ray micro-computed tomographic images and bone parameters of the distal sites of femurs in 9-week-old wild-type, Dcir−/− mice, Ifnγ−/−Dcir−/− mice and Ifnγ−/− mice. The error bars represent the means±s.e.m (n=4 to 5). *$P<0.05$; **$P<0.01$; n.s., not significant.

We next determined the cytokine property of T cells in Dcir−/− mice in the steady state. It was confirmed that T cells in the peripheral blood and in the brachial and axillary, but not the mesenteric lymph nodes in Dcir−/− mice resulted in the significant secretion of IFN-γ, and the serum concentration of IFN-γ in Dcir−/− mice tended to be higher than that of wild-type mice, indicating that the cytokine environment of Dcir−/− mice is inclined to favor an IFN-γ milieu (FIGS. 30 to 32). This led us to hypothesize that IFN-γ is a potent stimulator of osteoblast formation. The exogenous addition of IFN-γ augmented the alizarin red staining, an assessment of the ability of osteoblasts to mineralize, and the expression of osteogenic genes in a dose-dependent manner (FIGS. 33 and 34). The hypothesis is robustly proven in the histomorphometric analysis of Ifnγ−/−Dcir−/− mice and Ifnγ−/− mice whose bone structures were comparable with wild-type mice, indicating that in a steady state, IFN-γ acts on osteoblasts but not osteoclasts (FIG. 35). Collectively, the increased bone formation in Dcir−/− mice resulted from the systemic production of IFN-γ, in which the net balance of IFN-γ in vivo is skewed toward bone formation.

From these results, it is confirmed that the bone amount is increased in Dcir−/− mice, and that the increase is due to inclination of the cytokine environment of Dcir−/− mice to favor an IFN-γ milieu.

Example 1

Engagement of a receptor in its ligand is required for initiating signal cascades to exert the biological function thereof. Since the in vitro system of osteoclast formation is found only in BMMs, we assumed that the DCIR ligand could be expressed on BMMs or osteoclasts. While a portion of macrophages and osteoclasts were positive for DCIR-Fc staining, which occurs when the extracellular domain of a DCIR fuses with the Fc region of human IgG2, the binding was reduced with DCIRE197A/S199A-Fc, a mutant DCIR-Fc known to effect change in amino acids in CRD.

Figure 36:
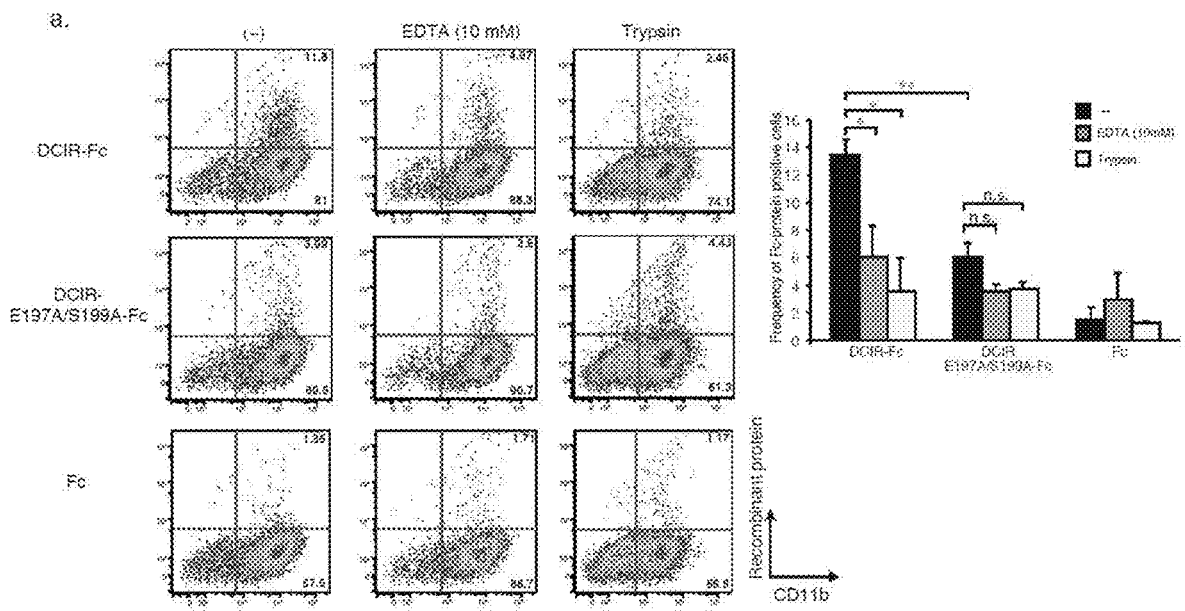
FIG. 36 shows the result of flow cytometric analysis of DCIR ligand expression in BMMs with or without EDTA treatment or with trypsin treatment. The error bars represent the means±s.e.m. of triplicate cultures. *$P<0.05$; **$P<0.01$; n.s., not significant.

Moreover, the binding of a DCIR-Fc was decreased by the effect of EDTA and trypsin, demonstrating that a DCIR interacts with glycoprotein in macrophages and osteoclasts in CRD- and $Ca^{2+}$-dependent manners (FIG. 36).

Figure 37:
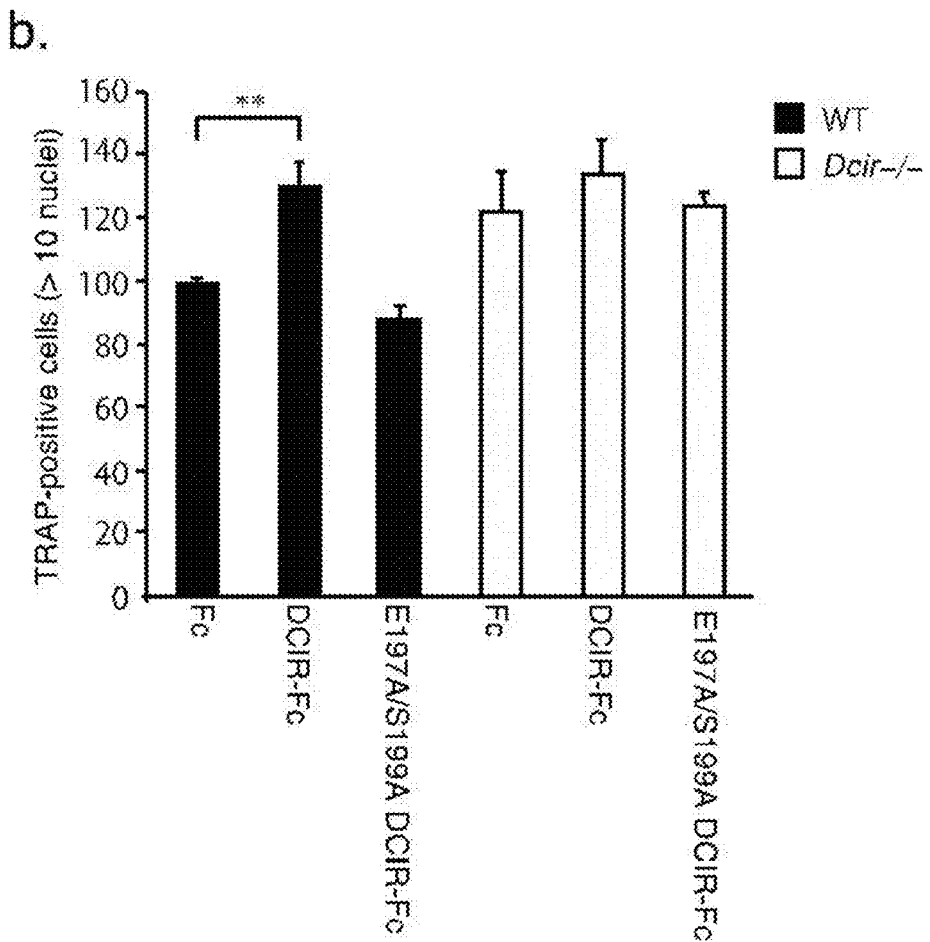
FIG. 37 shows that the osteoclast differentiation is blocked in a CRD-dependent manner. The error bars represent the means±s.d. of triplicate cultures, **$P<0.01$.

To investigate the functionality of a DCIR ligand in osteoclast formation, osteoclasts were formed in the presence of a DCIR-Fc. TRAP staining showed that multinucleated cells were elicited in significant amounts in wild-type BMMs (FIG. 37) and that osteoclast formation was unchanged in the presence of DCIRE197A/S199A-Fc (FIG. 37). These results indicate that a DCIR recognizes a ligand expressing in BMMs and suppress osteoclast formation, and this effect depend on CRD (FIG. 37). The presence of DCIR-Fc or a mutant DCIR-Fc did not affect the osteoclast formation in Dcir−/− BMMs, proving that the function is DCIR specific.

Figure 38:
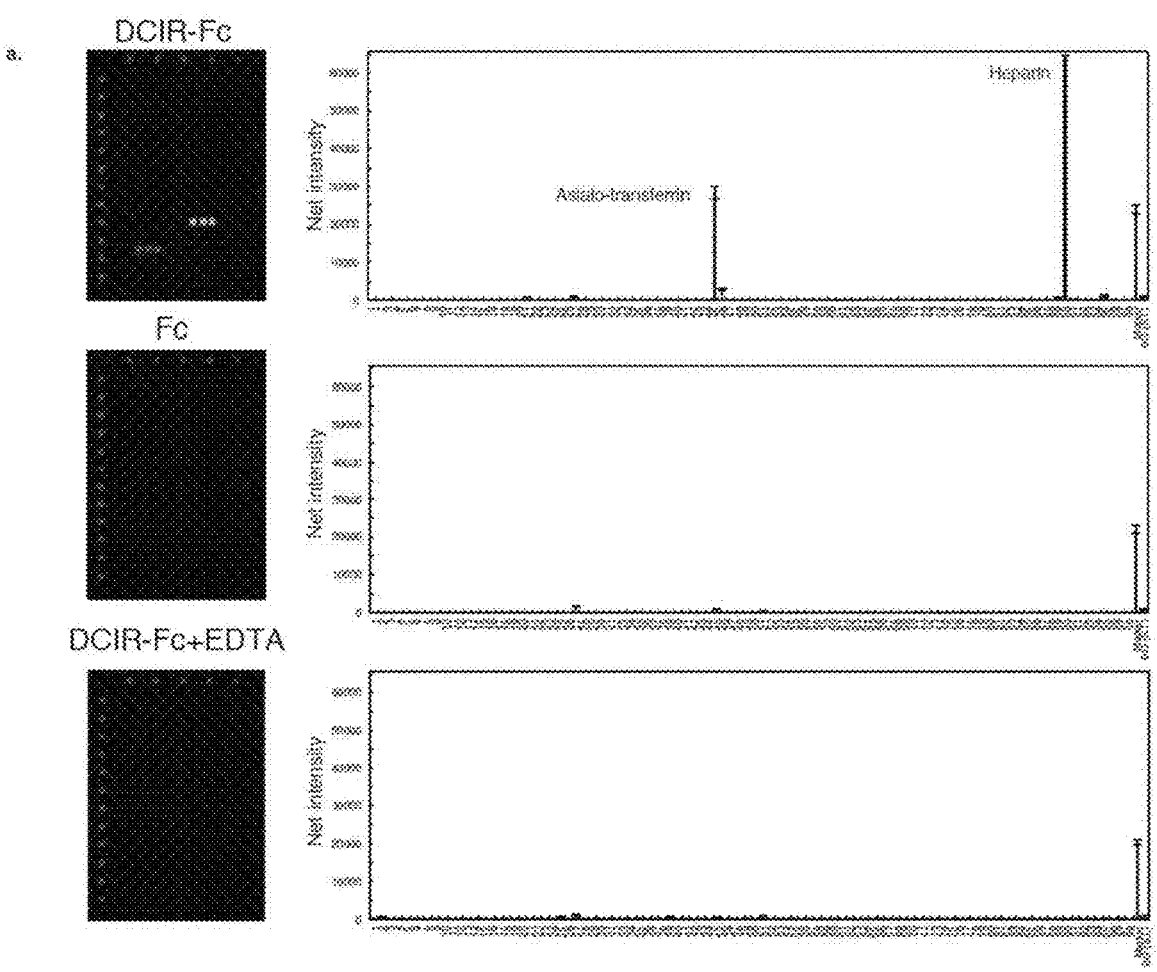
FIG. 38 shows the result of glycan array assay of DCIR-Fc binding to asialo-transferrin and heparin. DCIR-Fc and Fc proteins (10 μg/ml) were applied to epoxy-activated glass slides spotted in triplicate by glycoconjugates. The binding was detected by an evanescence-field fluorescence-activated scanner.
Figure 39:
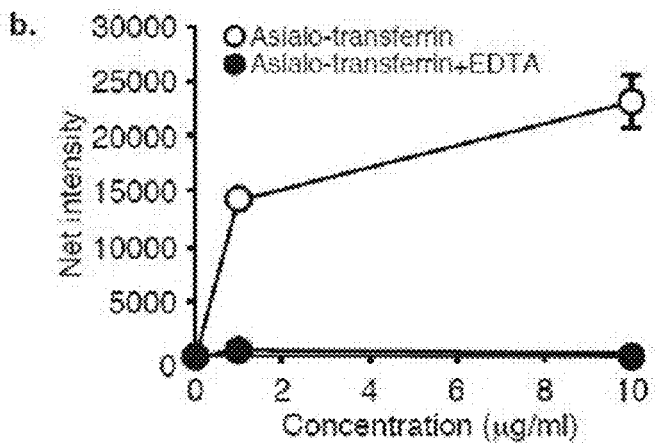
FIG. 39 shows the $Ca^{2+}$ dependency of binding of DCIR-Fc to asialo-transferrin and heparin-transferrin. The binding of indicated concentrations of DCIR-Fc to asialo-transferrin with or without EDTA (10 mM) was detected by an evanescence-field fluorescence-activated scanner.
Figure 39:
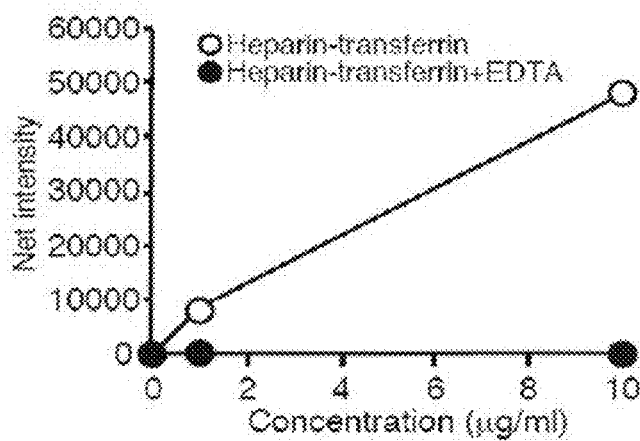
Figure 40:
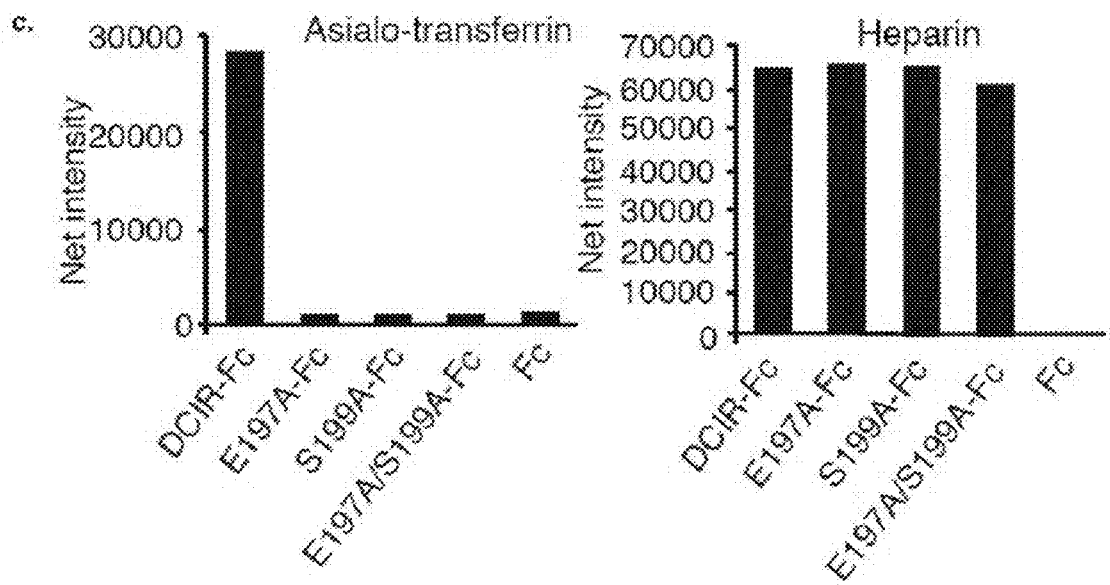
FIG. 40 shows that the binding of DCIR-Fc binding to asialo-transferrin is CRD-dependent, but not to heparin. The results of DCIR-Fc, DCIR-Fc mutants (E197A-Fc, S199A-Fc and E197A/S199A-Fc) and Fc as a negative control are shown.
Figure 41:
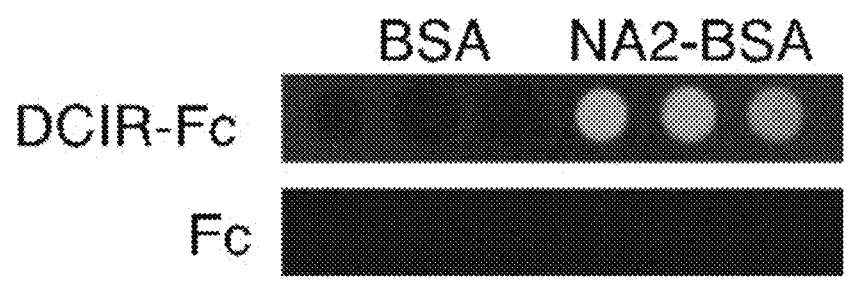
FIG. 41 is the result of glycan microarray assay showing that DCIR-Fc binds to asialo-biantennary N-glycan (NA2).
Figure 42:
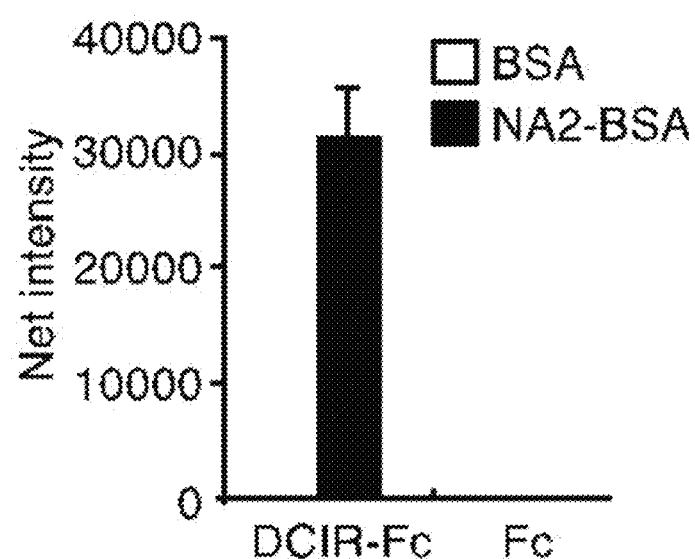
FIG. 42 shows the value of net intensity determined as the signal intensity minus background intensity. The error bars represent the means±s.d. of triplicate cultures.
Figure 43:
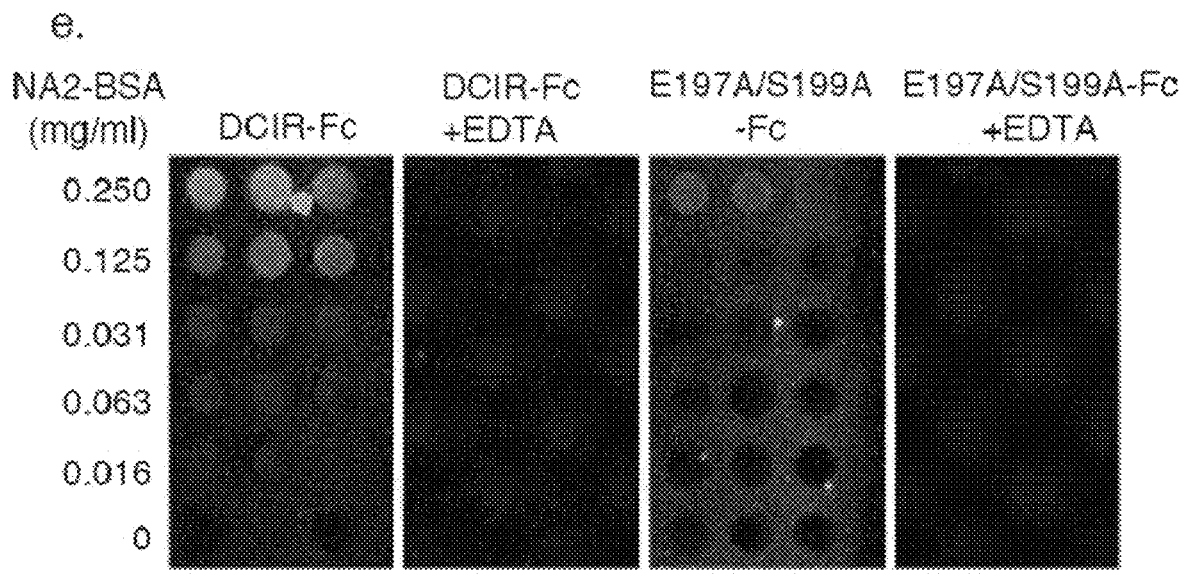
FIG. 43 shows the $Ca^{2+}$- and CRD-dependency of DCIR-Fc binding to NA2.
Figure 44:
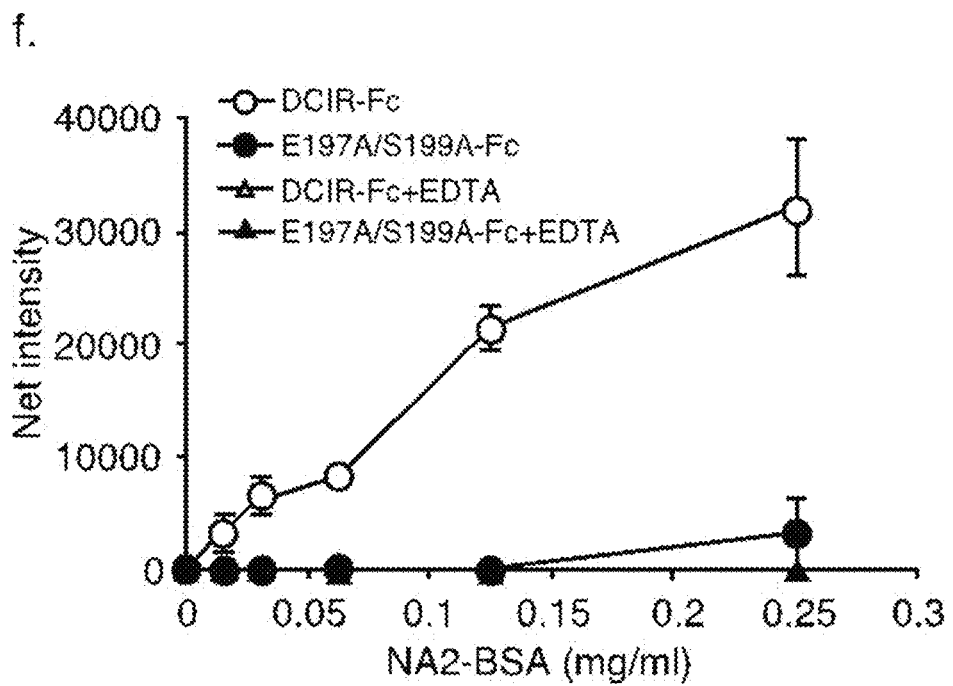
FIG. 44 shows the net intensity of CRD- and $Ca^{2\pm}$-dependent binding. The error bars represent the means±s.d. of triplicate cultures.

The effect of suppressing osteoclast formation by the addition of DCIR-Fc suggests the presence of an endogenous ligand. We detected a possible DCIR ligand by exploiting a glycan microarray with an evanescent-field fluorescence-assisted detection system. The glycan microarray revealed that a DCIR-Fc bound to asialo-transferrin and heparin in a $Ca^{2+}$-dependent way (FIGS. 38 and 39). While no binding of a mutant DCIR-Fc to asialo-transferrin was observed, the mutant DCIR-Fcs remained bound to heparin (FIG. 40). As the inhibition of osteoclast formation depended on CRD (FIG. 37), we focused our analysis on isolating the DCIR ligand on asialo-transferrin. Since the biantennary structure of N-glycan is predominant on transferrin, we assumed an asialo-biantennary N-glycan (NA2) as a DCIR ligand. It was found that a DCIR-Fc bound strongly to a NA2 (FIGS. 41 and 42), and that $Ca^{2+}$ and CRD were required for this bond to form (FIGS. 43 and 44).

Figure 45:
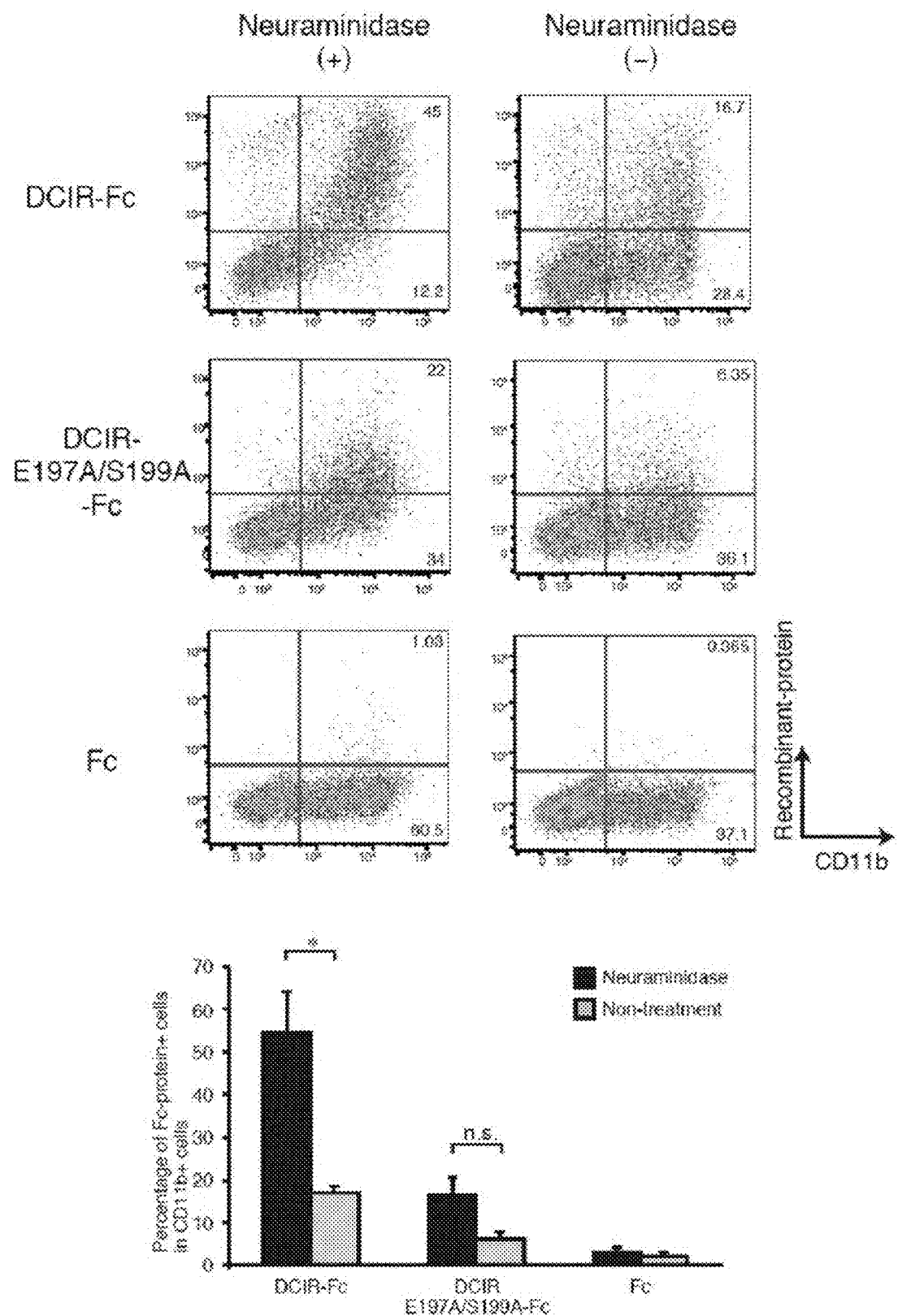
FIG. 45 shows the result of flow cytometric analysis of DCIR-Fc binding to neuraminidase-treated macrophages. The data are representative of three independent experiments. The error bars represent the means±s.d. of triplicate cultures. *$P<0.05$, **$P<0.01$, n.s. refers to not significant.
Figure 46:
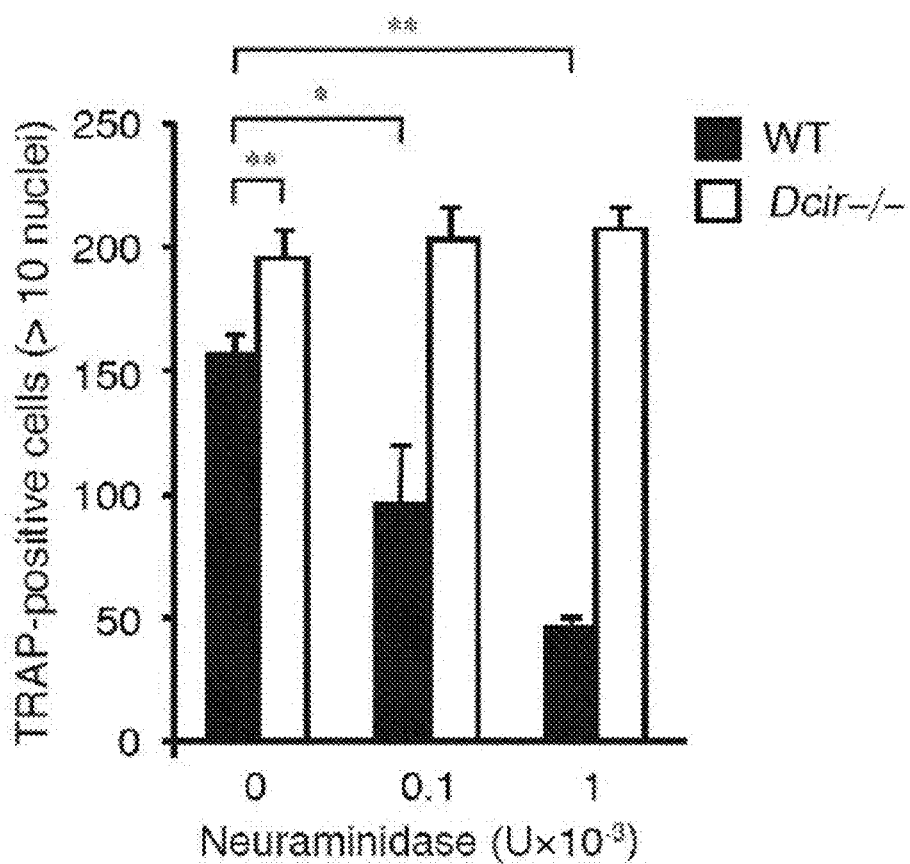
FIG. 46 shows the osteoclast formation in the presence of neuraminidase. The error bars represent the means±s.d. of triplicate cultures. *$P<0.05$, **$P<0.01$.
Figure 47:
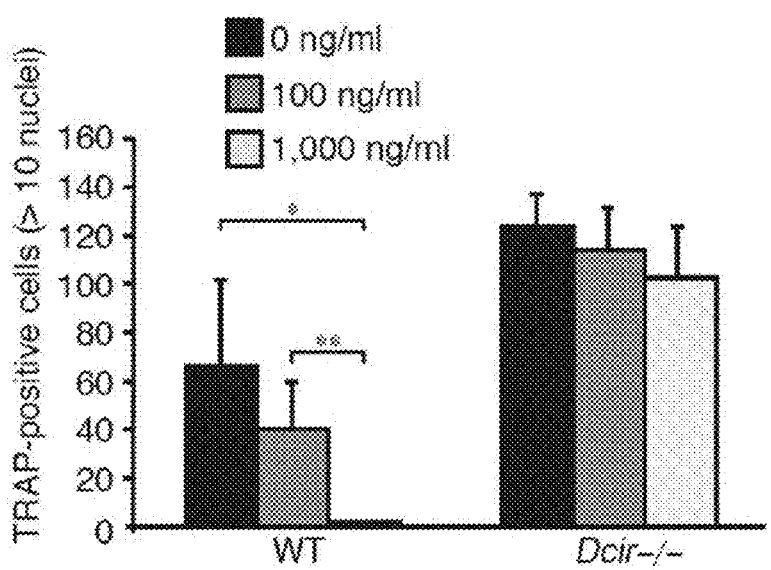
FIG. 47 shows that the osteoclast formation is inhibited by NA2 addition. The data are representative of three independent experiments. The error bars represent the means±s.d. of triplicate cultures. *$P<0.05$, **$P<0.01$.
Figure 48:
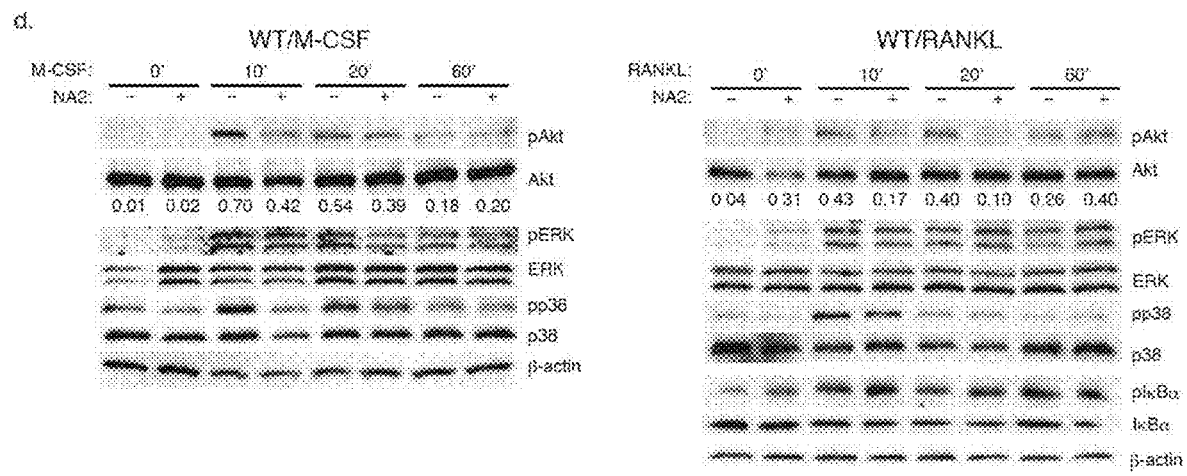
FIG. 48 shows the effect of NA2 on M-CSF- and RANKL-mediated signaling. Wild-type BMMs were subjected to pre-treatment with NA2 and stimulated with M-CSF or RANKL.
Figure 49:
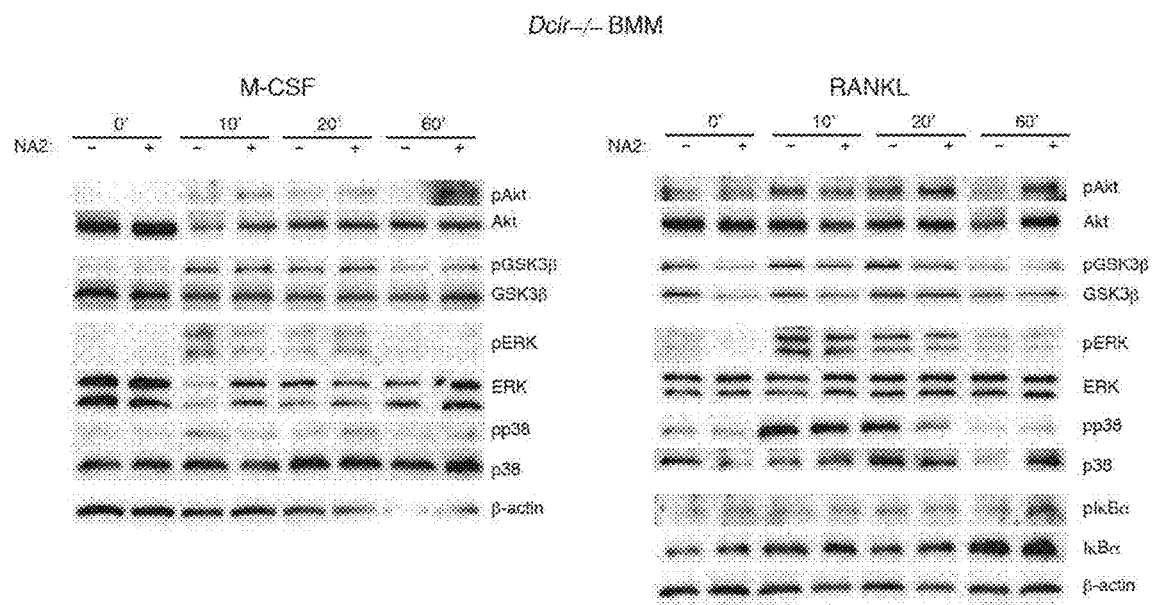
FIG. 49 shows that NA2 regulates M-CSF- and RANKL-mediated signals specifically through a DCIR. Dcir−/− BMMs were pre-treated with NA2 (1 μg/ml) at 37° C. for 6 hours in a serum-free medium, and were subjected to M-CSF (20 ng/ml) or RANKL (100 ng/ml) stimuli for the indicated time periods. The data are representative of at least three independent experiments.

Interestingly, neuraminidase treatment of BMMs enhanced the binding of DCIR-Fc (FIG. 45). While osteoclast formation was drastically inhibited in wild-type BMMs, no such effect was noted in Dcir−/− BMMs treated with neuraminidase (FIG. 46). The effect of a NA2 was a significant decrease in osteoclast formation in wild-type BMMs but not in Dcir−/− BMMs (FIG. 47). In addition, NA2 treatment resulted in a decrease of Akt phosphorylation in wild-type BMMs in response to M-CSF and RANKL (FIG. 48). In line with the phosphorylation profiles in Dcir−/− BMMs, NA2 treatment had no effect on MAPKs and IκBα upon M-CSF and RANKL stimuli (FIG. 49). These findings provide clear evidence that a NA2 is a functional DCIR ligand capable of suppressing osteoclast formation by downregulating M-CSF and RANKL signaling cascades.

From these results, it is confirmed that a NA2 is a ligand that binds to a DCIR in a specific and functional manner.

Example 2

Flt3L-induced dendritic cells (DCs) were prepared by the following process. Bone marrow cells were isolated from femurs of wild-type mice. Red blood cells were destroyed in a hemolysis buffer (consisting of 140 mM $NH_4Cl$ and 17 mM Tris-HCl, pH 7.2) for 10 minutes on ice. The cells were seeded at 1 million cells per well in 24-well plates in the presence of 100 ng/ml of recombinant human Flt3L in a medium containing 10% FBS, antibiotic mixtures, essential amino acids and 2-mercaptoethanol. At day 4, 100 ng/ml of recombinant human Flt3L (Milteny) was added in each well and further cultured for additional 4 days. At day 8, the cells were harvested and re-seeded at 500,000 cells per well in 96-well plates.

Figure 50:
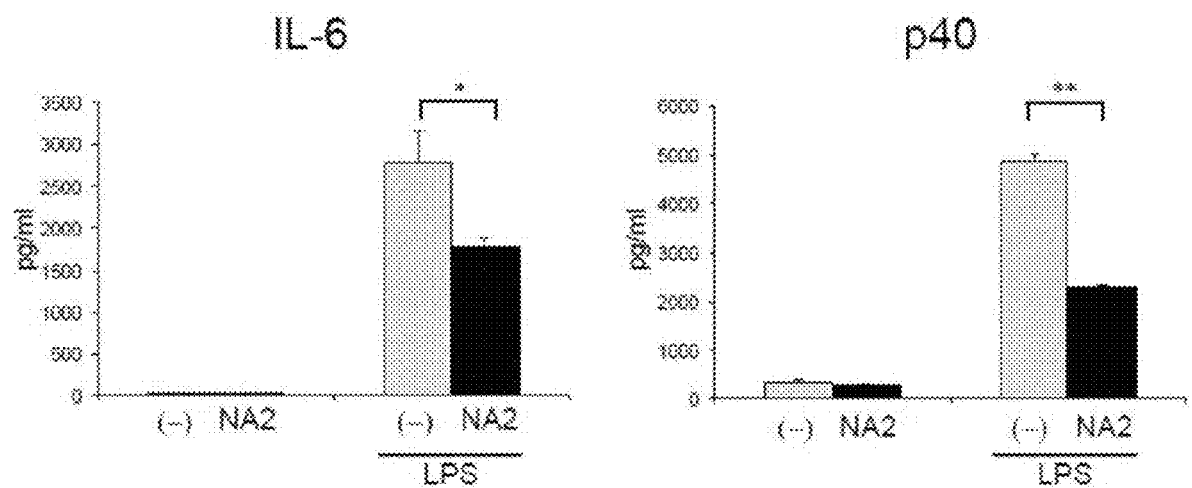
FIG. 50 shows the amount of pro-inflammatory cytokines when dendritic cells derived from bone marrow are stimulated by LPS with or without NA2.

The DCs thus obtained were activated with agonistic reagents (LPS) with or without 1 µg/ml of a NA2 for 24 hours. The supernatants were collected and the amounts of pro-inflammatory cytokines (IL-6 and p40) were determined by ELISA. As a result, the amount of pro-inflammatory cytokines were smaller when the DCs were stimulated by LPS in the presence of a NA2 than without the same (FIG. 50). In FIG. 50, the left-side two bars represent the amounts of pro-inflammatory cytokines without LPS stimulation, and the right-side two bars represent the amounts of pro-inflammatory cytokines with LPS stimulation, where the black bars represent the cases in the presence of a NA2.

From these results, it is confirmed that production of pro-inflammatory cytokines is suppressed by a NA2 binding to a DCIR.

<Materials and Methods>
(Preparation and Source of Mice)

Dcir−/− and Ifnγ−/− mice were prepared by a method as previously reported, and the mice were backcrossed to C57BL/6 at 12 generations. Rag2−/− mice were obtained from Central Institute for Experimental Animals. To generate Ifnγ−/−Dcir−/− mice, Dcir−/− mice were crossed into Ifnγ−/− mice in our mice facility. All the mice used in these experiments were male and 8 to 12 weeks old, and age- and sex-matched control C57BL/6J mice were purchased from Japan SCL, Inc. All the mice were housed in the animal care facility at the University of Tokyo or Tokyo University of Science, and were maintained following the guidelines of the Zoological Society of Japan. All animal experiments designed in experiments were accepted by the Animal Experiment Committee of the Institution of Medical Science in the University of Tokyo and Tokyo University of Science. The base sequence of the gene of murine DCIR corresponds to Gene ID: Clec4a2, the 273rd to 1061st base sequence of NCBI Accession No. NM001170332.

(Statistics)

The statistical differences between groups were determined using the two-tailed unpaired students' t-test (*P<0.05; P<0.01; *P<0.001; NS, not significant, in the paper). The difference between groups were considered statistically significant at P<0.05.

(Culture of Bone Marrow-Derived Macrophages and Osteoclasts)

To form M-CSF-dependent bone marrow-derived macrophages, BM cells were isolated by flushing the bone marrow cavity of femurs with α-minimal essential medium (α-MEM) (Gibco, trade name, Life Technologies), supplemented with penicillin (100 units/ml), streptomycin (100 µg/ml) and 10% heat-inactivated fetal bovine serum. Red blood cells were destroyed in a hemolysis buffer (consisting of 140 mM $NH_4Cl$ and 17 mM Tris-HCl, pH 7.2) for 10 minutes on ice, and the treated cells were pre-incubated in a 100 mm dish for 1 hour. The non-adherent cells (hematopoietic cells) were harvested and seeded at 50,000 cells per well in 96-well plates in the presence of 20 ng/ml of recombinant human M-CSF (R&D Systems) for 2 days. The cells proliferated in response to M-CSF were defined as BMMs. To generate osteoclasts, the BMMs were further cultured in 20 ng/ml of M-CSF and 100 ng/ml of human recombinant soluble RANKL (Oriental Yeast), and the culture medium was replaced every two days. For matured macrophages, the BMMs were incubated in 20 ng/ml of M-CSF for 6 days and the medium was changed every two days. In some experiments, the BMMs cultured in a 100 mm dish were dissociated with Cell Dissociation Solution Non-enzymatic 1× (Sigma-Aldrich) and an equal number of BMMs was re-plated to induce osteoclast formation.

(Measurement of Osteoclast Formation by TRAP Staining)

Adherent cells were fixed in 10% formalin for 3 minutes, followed by further fixation in a fixative buffer consisting of 50% ethanol and 50% acetone for 1 minute. The cells were stained with Naphthol AS-MX phosphate (Nacalai Tesque) and Fast-red (Nacalai Tesque) for 10 to 15 minutes at room temperature (RT), and washed with water three times. TRAP-positive cells with more than 3 or 10 nuclei were counted as multinucleated osteoclasts.

(Retroviral Infection on Bone Marrow Cells)

Murine DCIR cDNA was amplified using the following primers: sense 5'-cgggatcccaccatggcttcagaaatcacttatg (sequence No. 1) and antisense 5'-cggaattctcataagtttattttcttca (sequence No. 2). The PCR product was cloned into pMXs-IRES-Puro (kindly provided by Kitamura, T., The University of Tokyo) via the BamHI and EcoRI site. The pMXs vector was isolated from E.coli (DH5α). DCIR Y/F mutation was generated using a KOD-Plus-Mutagenesis Kit (TOYOBO, Japan). In brief, to replace the tyrosine in the ITIM of DCIR to phenylalanine, we designed a forward primer 5'-cactTttgcagaagtgaagttcaagaatgaatc (sequence No. 3, adenosine was changed into capital T) and a reverse primer 5'-atttctgaagccatggtgggatccttggttaac (sequence No.

4, adenosine was changed into capital T). Inverse PCR was performed using the pMXs vector as a template, which was digested by Dpn I capable of digesting methylated DNA from typical E.coli cell lines. Non-digested PCR products were self-ligated by T4 polynucleotide kinase and ligase at 16° C. for 1 hour. A plat-E packaging cell line (also provided by Kitamura, T) was cultured in 10% FBS α-MEM, and split every second day at a ratio of 1:5. The retroviral vectors were transfected in Plat-E cells by Lipofectamine 2000 (Invitrogen). Eight hours after the incubation, the medium was changed and further incubated for 24 hours. The retroviral supernatant was collected and frozen at −80° C. until it was used. To retrovirally transduce DCIR and DCIR mutant BMs, non-adherent bone marrow cells were cultured in 100 μl of medium containing 20 μl of retroviral supernatant, and the medium was replaced every two days.

(Tritium Thymidine Incorporation Assay)

BMMs were harvested using Cell Dissociation Solution Non-enzymatic 1×(Sigma-Aldrich) and plated at 300,000 cells per well in 96-well plates in the presence of various concentrations of M-CSF. Two to 3 hours later, 1.0 μCi of [3H] thymidine (PerkinElmer) was added and the BMMs were further incubated for 48 hours at 37° C. The cells were passed through glass fiber filters with the Skatron microplate washer supernatant collection system (Molecular Device) and the incorporation of [$^3$H] thymidine into DNA was determined with the MicroBeta microplate counter system (PerkinElmer Inc.)

(FACS Analysis)

BM cells and peripheral blood mononuclear cells (PB-MCs) underwent blood cell lysis with a hemolysis buffer (consisting of 140 mM $NH_4Cl$ and 17 mM Tris-HCl, pH 7.2) on ice. The BMMs and PBS were detached and washed with a FACS buffer consisting of 2% FBS in PBS to remove serum components. The Fc receptors on these cells were blocked with 2.4G2, a Fc receptor blocker, at 4° C. for 10 minutes. These cells were washed twice with a FACS buffer and incubated with fluorescence-conjugated antibodies for 30 minutes on ice. The following commercially available antibodies were used: APC- or PE-CD11b (BioLegend), FITC-Lytic (BioLegend), APC-c-Fms (BioLegend), biotin-RANK (eBioscience) and PE-Clec4a (R&D Systems Inc.) For staining intracellular molecules, FITC-CD3, Pacific Blue-CD4, APC-CD8, BV510-CD11b and PE-IFN-γ (BioLegend) were used. To form a protein complex consisting of Fc-protein and anti-IgG antibodies to detect a DCIR ligand, 10 μg/ml of DCIR-Fc-protein, mutated DCIR-Fc-protein, or Fc-protein were incubated with 5 μg/ml of FITC-conjugated anti-human IgG (Jackson ImmunoResearch Laboratories) in a buffer containing calcium and magnesium (2 mM calcium chloride, 2 mM magnesium chloride, 0.5% BSA in Tris-buffered saline) for 15 minutes at RT. Macrophages and osteoclasts were stained with the protein complex for 1 hour at 4° C., followed by gentle washing with the $Ca^{2+}/Mg^{2+}$ buffer. Flow cytometry was performed on FACSCanto II (Becton Dickinson) and analyzed using Flowjo software (Tree Star) For intracellular staining, cells were first stained with 2.4G2, followed by FITC-CD3 staining for a surface antigen before fixation. After washing with a FACS buffer, fixation/permeabilization buffer (eBioscience) was added and left at 4° C. for 60 minute. After centrifugation, the fixation/permeabilization buffer was decanted and the cells were washed twice with a 0.1% saponin-containing FACS buffer. These cells were stained with primary antibodies for surface antigens and intracellular molecules, which were diluted in the 0.1% saponin buffer.

(Quantitative RT-PCR and Conventional PCR)

Total RNA was extracted from the BMMs and the osteoclasts using the GenEluteTM Mammalian Total RNA Miniprep kit (Sigma-Aldrich). Quantification of total RNA was performed using NanoDrop. One μg of total RNA was reverse-transcribed using Superscript II Reverse Transcriptase (Invitrogen) to synthesize $1^{st}$ cDNA. Quantitative PCR was carried out in a total reaction volume of 10 μl including 5 ng equivalent to total RNA, SYBR Green I (TAKARA bio), and a set of forward and reverse primers (Operon) in duplicate or triplicate samples. Quantification was performed on CFX384™ Real-Time system (Bio-Rad Laboratories) Cycling program was 1 cycle of 95° C. for 1 minute, following 44 cycles of a set of 95° C. for 3 seconds and 60° C. for 30 seconds, and 1 cycle of 65° C. for 5 seconds and 95° C. The following primers were used: DCIR sense 5'-cctggtgattctatgctgtggt-3' (sequence No. 5), anti-sense 5'-gtcagaagagagccttgttccttc-3' (sequence No. 6); GAPDH sense 5'-ttcaccaccatggagaaggc-3' (sequence No. 7), antisense 5'-ggcatggactgtggtcatga-3' (sequence No. 8). The final concentration of the primers was 400 nM. GAPDH was used as the internal housekeeping gene. The target genes and the housekeeping gene were quantified simultaneously in one plate, with water samples as the negative reference. The difference in RNA quality and initial quantity between the samples was normalized to GAPDH. The relative expression of the targeted gene was calculated from the following equation: $2^{-dCt}$, where dCt=average Ct for the gene of interest−average Ct for the housekeeping gene. The fold change of a targeted gene at days 3 and 4 relative to a sample at day 2 was determined by the following: $2^{-ddCt}$, where ddCt=(average Ct for gene of interest−average Ct for the gene of a housekeeping gene) each sample at days 3 and 4−(average Ct for gene of interest−average Ct for the housekeeping gene) sample at day 2. The standard deviation was calculated according to a mathematical method described in earlier reports. RT-PCR was performed in 20 μl of reaction volume with Ex-taq (Takara bio). A primer set for amplifying DCIR was sense 5'- catttcccttatctcgccctgg-3' (sequence No. 9) and anti-sense 5'- gcatgagtgtccaagatcc-3' (sequence No. 10), which amplified a 686 bp product. The PCR reaction was run in the following program: 30 cycles of 98° C. for 10 seconds, 55° C. for 30 seconds, and 72° C. for 1 minute. GAPDH was used as an internal control.

(Biochemical Analysis)

For western blotting of M-CSF- and RANKL-mediated signals, BMMs were re-plated in a 12-well plate at 250,000 cells per well in the presence of 5 ng/ml of M-CSF. 24 hours after the culture, the BMMs were left in a serum-free medium without M-CSF for 6 hours before stimulation. The cells were activated with 20 ng/ml of M-CSF or 100 ng/ml of RANKL for predetermined periods. The cells were dissolved to prepare cell lysates in 1% NP-40 (consisting of 10 mM Tris-HCl, pH 7.5, 100 mM NaCl, 5 mM $MgCl_2$ with a proteinase inhibitor cocktail (Thermo Fischer Scientific) and a phosphatase inhibitor cocktail (Roche). The lysates were kept on ice for 10 minutes and clarified by centrifugation at 15,000 rpm for 10 minutes. Equal aliquots of lysates were loaded in SDS-polyacrylamide gels and separated at 230 V for 30 minutes. A gel was electrophoretically transferred onto a PVDF membrane at constant 230 mA for 25 minutes per membrane in a semidry system (Bio-Rad Laboratories). The membranes were blocked by 5% BSA (Sigma-Aldrich) in TBS containing 5% Tween 20 for 1 hour at RT and incubated with primary antibodies at 4° C. for overnight, followed by probing with HRP-conjugated secondary antibodies. The membrane was subjected to ECL Prime Western Blotting Detection System (GE Healthcare) to visualize signals of protein.

(Generation of Fc-Fused DCIR Protein)

Murine DCIR cDNA, covering the extracellular domain (EC) from 70 to 238 at the amino acid level, was subcloned into pFUSE-hIgG2-Fc2 vector (Invitrogen) at Bgl II site. cDNA coding the extracellular domain was generated with a primer set; sense 5'-ataagatctcaaaagtactctcaacttctt-3' (sequence No. 11) and anti-sense 5'-ataagatcttaagtttattttcttcatc-3' (sequence No. 12). Site-directed mutations of the CRD domain, in which glutamic acid and serine were replaced to alanine, were established by KOD-Plus-Mutagenesis Kit (TOYOBO). The following primer set was used for the mutagenesis: E197A sense 5'-AATGGTGCTCCCAGCA-GTGGCAATGAA-3'(sequence No. 13), anti-sense 5'-TG-TAAGACCGTGTTACCACGAGGGTCA-3'(sequence No. 14); S199A sense 5'-GAGCCCGCTAGTGGCAAT-GAAAAATGT-3'(sequence No. 15), anti-sense 5'-ACCGT-GTTACCACTCGGGCGATCACCG-3' (sequence No. 16); E197A/S199A sense 5'-GGTGCTCCCGCTAGTGGCAAT-GAAAAATGTGCT-3' (sequence No. 17), anti-sense 5'-TAGTGTAAGACCGTGTTACCACGAGGGCGATCA-3'(sequence No. 18).

Plasmid vectors for DCIR-Fc (the EC of mDCIR), mutant DCIR-Fc (inactive form of CRD domain), and Fc-protein (constant region of immunoglobulin) were prepared, respectively. The plasmids were transferred into HEK293T cells by Lipofectamine LTX (Invitrogen), and the cells were incubated in Opti-MEM (Invitrogen) for 15 days and the medium was changed every 3 days. The Fc-chimeric proteins were purified from collected supernatant by affinity chromatography on Protein A-Sepharose (GE Healthcare UK)

(Functional Assay of DCIR Ligand)

Wild-type and Dcir−/− BMMs were induced to differentiate osteoclasts in the presence of M-CSF and RANKL. NA2, purchased from GlycoTech (Gaithersburg) was applied at the beginning of the culture of non-adherent BM cells, and consistently added each time the medium was replaced. The number of osteoclasts was determined by TRAP staining. To estimate the bio-activity of NA2, the BMMs were treated with or without NA2 for 6 hours before applying M-CSF (20 ng/ml) or RANKL (100 ng/ml) stimuli. Cell lysates were analyzed by western blotting to detect the phosphorylation levels of signal components.

(Neuraminidase Treatment)

After the culture for 6 days, the BMMs were harvested using Cell Dissociation Solution Non-enzymatic 1× (Sigma-Aldrich) and re-suspended in a TSA buffer (TBS containing 2 mM $CaCl_2$, 2 mM $MgCl_2$ and 0.5% BSA). The cells were treated with 0.5 μl of neuraminidase (Roche) per million cells at 37° C. for 30 minutes. The cells were washed with the TSA buffer and then subjected to FACS analysis. To measure the effect of the removal of sialic acid on osteoclast formation, osteoclasts were induced from non-adherent BM cells in the presence of 1 μl of neuraminidase (Roche). Neuraminidase was replaced when the culture medium was changed every second days.

(Calcein Labeling)

Dynamic histomorphometric analysis of bone formation was carried out by Kureha Special Laboratory. Body weights of wild-type and Dcir−/− mice at 8 weeks of age were measured and the mice were intraperitoneally administrated with 16 mg/kg (body weight) of calcein (Nacalai Tesque) twice at intervals of two days. The mice were sacrificed at day 2 after the last injection of calcein and the mouse tibiae were cleaned of soft tissue and muscle, and then fixed in 70% ethanol for one week with the ethanol replaced every day. The mineralization regions were stained as green lines. The undecalcified bone tissues were placed in methyl benzoate for 15 minutes to facilitate infiltration of glycol methacrylate (GMA) into the tissues and were immersed in 5% methyl benzoate in GMA at 4° C., which was replaced three times in a period of two hours. Then, the bone tissues were embedded in GMA. Sections of tibiae of 3 μm in thickness were prepared using a microtome (Sakura Fintek) and fluorescence was detected at the mineralization front. For dynamic bone formation, the mineralizing surface (mineralization surface/bone surface [MS]/[BS]; %), mineral apposition rate ([MAR]; μm/day), and bone formation rate ([BFR]/[Bs]; $μm^3/μm^2/day$) were determined at 400-fold magnification using an image analyzer (System supply)

(Bone Histomorphometric Analysis)

Histomorphometric analysis of the murine tibiae was performed by Kureha Special Laboratory. The bones of wild-type and Dcir−/− mice were isolated from 5 to 6 mice per group of 8 week old mice, and fixed with 70% ethanol. To measure the histomorphometric parameters of the bone structure, sections of GMA-embedding femur tissues of 3 μm in thickness were stained with toluidine blue. The trabecular bone parameter was determined in an area of the secondary spongiosa of 1.05 mm in width, in a distal direction from the point of 0.3 mm apart from the growth plate. The trabecular bones in metaphysis were examined with a HistometryRT CAMERA. For assaying the osteoclast number ([Oc.N]/100 mm) and osteoclast surface area ([Oc.S]/[BS]; %), osteoclasts were defined as cells with more than one nucleus that formed resorption lacunae at the surface of the trabeculae. The parameters of bone remodeling, including the osteoblast number ([Ob.N]/100 mm) and osteoblast surface area ([Ob.S]/[BS]; %), were measured in toluidine blue-stained sections.

(Micro-Computed Tomography (Micro-CT) Analysis)

The structural properties of wild-type and Dcir−/− mice were determined by a high resolution micro-CT system. In brief, the femoral cancellous bone with a length of 1.814 mm of a cross-section area at the distal end of femoral metaphysis was scanned with a micro-CT system (Scan Xmate-L090, Comscantecno) Then, 3D image analysis was carried out using TRI/3D BON software (Ratoc System Engineering) The trabecular bone mineral density was characterized by calculating the bone volume density (bone volume [BV]/tissue volume [TV]), trabecular thickness (Tb.Th.=2×BV/bone surface [BS]), trabecular number (Tb.N=(BV/TV)/Tb.Th.), trabecular separation (Tb.Sp=1/Tb.N·Tb.Th.) and trabecular spacing (Tb.Spac=1/Tb.N). The trabecular number was defined as the number of trabecular bone cells.

(Measurement of IFN-γ-Producing T Cells in Peripheral Blood)

Whole blood was obtained by cardiac puncture with a 21-gauge needle-attached syringe containing a quantity of heparin (Mochida Pharmaceutical) from mice under anesthesia. The blood samples were mixed with ten volumes of hemolysis buffer and left on ice for 10 minutes, followed by centrifugation at 1500 rpm at 4° C. for 5 minutes to collect mononuclear cells. The hemolysis buffer treatment was repeated three times. PBMCs underwent stimulation for 5 hours with phorbol myristate acetate (final concentration; 500 ng/ml) plus ionomycin (final concentration; 50 ng/ml) with brefeldin A (final concentration; 10 μg/ml) during the entire incubation period. IFN-γ secretion of PBMCs was detected by intracellular molecular staining and flow cytometric analysis.

(Primary Murine Osteoblast Culture)

Calvarial cells were prepared by sequential digestion followed by a standard method. Briefly, calvavria from 1 to 2-day old neonates were surgically isolated and adherent mesenchymal tissues were trimmed. The neonatal calvaria underwent a first digestion with a degrading solution containing 0.1% collagenase (Wako Pure Chemical Industries) and 0.1% dispase (Roche Diagnostics Japan) for 10 minutes at 37° C. with agitation. The solution was discarded to remove debris, and the remaining calvaria were further digested by the same degrading solution for 1 hour at 37° C. The cells isolated from the serial digestions were suspended in an a-MEM containing 10% FCS, penicillin (100 units/ml) and streptomycin (100 μg/ml), and plated at the concentration of 200,000 cells/well in 12-well plates. Two days after the culture, the cells were incubated in an osteogenic medium (α-MEM supplemented with 10% FBS, 50 μg/ml ascorbic acid (Sigma-Aldrich), 10 mM β-glycerophosphate (Calbiochem) and antibiotics) for 14 days or 21 days, with the medium replaced every 3 days for the entire duration.

(Evaluation of IFN-γ Effect on Osteoblast Formation)

Murine osteoblasts were cultured and differentiated according to the protocol as mentioned above. The primary murine osteoblasts were cultured in the presence of recombinant murine IFN-γ (PeproTech) from the start of the culture, and IFN-γ was added each time when the osteogenic medium was replaced.

(Magnetic Cell Sorting)

Calvaria cells were obtained from neonates by a process as described above. Red blood cells were lysed in a hemolysis buffer for 10 minutes at 37° C. The remaining cells were re-suspended in 90 μl of autoMACS Running Buffer (Miltenyi Biotec) per ten millions total cells and incubated with 10 μl of CD11b MicroBeads (Miltenyi Biotec) per ten millions total cells for 15 minutes at 4° C. The cells were washed with a MACS buffer and re-suspended up to $10^8$ cells in 500 μl of autoMACS Running Buffer, and passed through a 75 nylon mesh (75×75 μm mesh) to remove cell clumps. CD11b-positive and -negative fractions were separated by an auto MACS Pro separator (Milteny Biotec), and these cells were used as OsteoMacs or primary osteoblast cells, respectively.

(Mineralization Nodule Formation Assay)

The mineralization formation of osteoblastic cells was detected by the von Kossa method and staining with alizarin red S (sodium alizarin sulphonate). For the von Kossa method, the osteoblast cultures were fixed in 10% formalin for 10 minutes at RT. After rinsing, the fixed cells were exposed to bright sunlight in 5% silver nitrate solution for 30 minutes, followed by a 5% sodium thiosulfate wash. The mineralized nodules were visualized as dark brown or black spots. In alizarin red S staining, the osteoblasts were fixed with 10% formalin for 10 minutes at RT and stained with 1% alizarin red S (pH 4.2) for 10 minutes at RT. After washing with distilled water to remove excess dye, the mineralized nodules were seen as dark red spots. The cell images were captured by a GT-X770 image scanner (Seiko Epson).

(Co-Culture of Calvarial Cells and BM Cells)

Primary calvarial cells were enzymatically harvested and seeded at 200,000 cells/well in 12-well plates in α-MEM containing vitamin D3 ($10^{-8}$ M) and prostaglandin E2 ($10^{-6}$ M) for 24 hours. A 10-fold number of non-adherent bone marrow cells were co-cultured with primary osteoblasts for 7 days, and the medium was changed every three days.

(Pit Formation)

Osteoclasts were generated in a 5-day culture in a 100 mm dish as described above. The osteoclasts were enzymatically harvested and reseeded at a concentration of 20,000 cells per well in an Osteo Assay plate (Corning) in the presence of M-CSF and RANKL. After 3 days, the cells were removed by ultrasonic destruction for 30 seconds in a 1 M ammonia solution. The entire surface of the calcium phosphate-coated well was captured with a microscope (Keyence) and the images were analyzed with ImageJ to examine the total resorbed area.

(Adhesion Assay)

A 96-well plate was coated with 10 mg/ml fibronectin (Sigma-Aldrich) and left overnight at 4° C. The wells were washed twice with PBS, and the BMMs in 2 days culture were seeded onto the plates at 50,000 cells for 2, 5 or 10 minutes with or without M-CSF (20 ng/ml). To determine adhesion activity, the cells were washed twice with DMEM, fixed in methanol for 2 minutes, and stained with 0.5% crystal violet in distilled water for 5 minutes. After washing five times with distilled water, 100 ml of 1% SDS was added to each well to solubilize the dye, and absorbance was measured at 595 nm.

(Apoptotic Assay)

BMMs cultured for 2 days were incubated in M-CSF in combination with 100 ng/ml of RANKL, in 48-well plates at 10,000 cells per well. The medium was changed every 2 days. At days 7 and 8 from the beginning of the culture, the medium was carefully removed and cell lysates were prepared with a cell lysis buffer of a cell apoptosis detection kit (Cell Death Detection ELISA, Roche Molecular Biochemicals) for 30 minutes at RT. As a positive control of cell apoptosis, all cytokines were removed from the wells of 8-day culture during the last 6 hours. 20 μl of the supernatant were analyzed by ELISA to determine the magnitude of apoptosis.

(Primer Sets for Quantitative RT-PCR)

The following primers were used for detecting transcripts in osteoclasts:

```
Acp (TRAP) sense
                          (sequence No. 19)
5'-cagcagcccaaaatgcct-3', anti-sense
                          (sequence No. 20)
5'-ttttgagccaggacagctga-3';

NFATc1 sense
                          (sequence No. 21)
5'-gccaagtaccagctttccag-3', anti-sense
                          (sequence No. 22)
5'-agggtcgaggtgacactagg-3';

Calc (Calcitonin R) sense
                          (sequence No. 23)
5'-gcctccccatttacatctgc-3', anti-sense
                          (sequence No. 24)
5'-ctcctcgccttcgttgttg-3';

Nfatc1 sense
                          (sequence No. 25)
5'-gccaagtaccaggtttccag-3', anti-sense
                          (sequence No. 26)
5'-agggtcgaggtgacactagg-3';

cSrc sense
                          (sequence No. 27)
5'-gaacccgagagggaccttc-3',
```

-continued

```
anti-sense
                                      (sequence No. 28)
5'-gaggcagtaggcaccttttgt-3';

Pirb sense
                                      (sequence No. 29)
5'-agccagaaaacaaggctgaa-3', anti-sense
                                      (sequence No. 30)
5'-ggctgggtgtccagtagtgt-3';

Sirpa sense
                                      (sequence No. 31)
5'-gtaggtgcgactgggatgtt-3', anti-sense
                                      (sequence No. 32)
5'-agtgaggccaactcagccta-3'
```

The following primers were used for detecting transcripts in osteoblasts:

```
nfsf11 (RANKL) sense
                                      (sequence No. 33)
5'-cagcatcgctctgttcctgta-3', anti-sense
                                      (sequence No. 34)
5'-ctgcgttttcatggagtctca-3';

Tnfsf11b (OPG) sense
                                      (sequence No. 35)
5'-gggcgttacctggagatcg-3', anti-sense
                                      (sequence No. 36)
5'-gagaagaacccatctggacattt-3'
```

The quality and the quantity of mRNA were normalized to GAPDH.

(Glycan Array Assay)

The glycan-protein interaction was detected in a glycan microarray with an evanescent-field fluorescence-assisted detection system. Briefly, glycan probes, including glycoproteins and glycoside-polyacrylamide (PAA), were immobilized on microarray-grade epoxy-activated glass slides (Schott AG) in triplicate spots using a noncontact microarray printing robot, MicroSys 4000 (Genomic Solutions). The glass slides were incubated at 25° C. for 3 hours and washed with a reaction buffer consisting of 25 mM Tris HCl (pH 7.4) containing 0.8% NaCl, 1% (v/v) Triton-X, 1 mM $MnCl_2$, and 1 mM $CaCl_2$ to remove immobilized materials, followed by blocking in TBS (25 mM Tris-HCl (pH 7.4) with 0.8% NaCl and 1% BSA) at 20° C. for 1 hour. A protein complex of DCIR-Fc, mutant DCIR-Fc, or Fc with Cy3-labelled anti-human Fc antibodies was formed in a reaction buffer at RT by 20 minutes kept in the dark.

The protein complex was applied to a glass slide at 100 μl per chamber, and was incubated at 20° C. for 3 hours. Without washing, the binding was detected with an evanescent-field activated fluorescence scanner, SC-Profiler (GP Bioscience), and the data was analyzed by the Array Pro analyzer Ver. 4.5 (Media Cybernetics, Inc.) Subtracted raw intensity from background intensity is net intensity, which is presented as the average±s.d. of triplicate spots.

(Serum Collection)

Whole blood was obtained from a mouse by cardiac puncture under the anesthesia condition. The blood samples were left overnight to clot at 4° C., and centrifuged at 3,000 rpm for 10 minutes to separate a serum from coagulated blood. The serum was collected and stored at −80° C. until the assay. The serum amount of IFN-γ was determined with ELISA kit for IFN-γ (Mabtech).

The disclosure of Japanese Patent Application No. 2014-143491 is incorporated herein in its entirety. All publications, patent applications, and technical standards mentioned in this specification are herein incorporated by reference to the same extent as if each individual publication, patent application, or technical standard was specifically and individually indicated to be incorporated by reference.

The invention claimed is:

1. A method for activating dendritic cell immune receptor (DCIR), comprising causing a dendritic cell immune receptor activator to contact DCIR on an osteoclast cell,
the dendritic cell immune receptor activator comprising a compound having a sugar chain as an active ingredient, the sugar chain having a basic structure represented by the following formula:

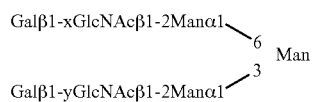

wherein, in the formula, a sialic acid does not exist at two non-reducing terminals, and each of x and y independently represents 3 or 4.

2. The method for activating DCIR according to claim 1, wherein the method inhibits osteoclast formation.

3. The method for activating DCIR according to claim 1, wherein the method inhibits dendritic cell differentiation/proliferation.

4. The method for activating DCIR according to claim 1, wherein the method inhibits cytokine production.

5. The method for activating DCIR according to claim 4, wherein the cytokine is selected from the group consisting of IFN-γ, IL-6, IL-12, IL-23, IL-1, IL-17 and IL-17F.

6. A therapeutic method for treating a disease in which dendritic cell immune receptor (DCIR) is involved, comprising administering a DCIR activator to a patient having a bone metabolism disease, an autoimmune disease or an allergy disease,
the dendritic cell immune receptor activator comprising a compound having a sugar chain as an active ingredient, the sugar chain having a basic structure represented by the following formula:

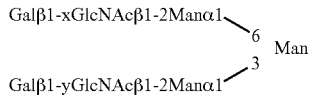

wherein, in the formula, a sialic acid does not exist at two non-reducing terminals, and each of x and y independently represents 3 or 4.

7. The method of claim 6 wherein the disease is selected from the group consisting of a bone metabolism disease, an allergy disease, arthrorheumatism, multiple sclerosis, Guillain-Barre syndrome, Goodpasture's syndrome and colitis ulcerosa.

* * * * *